United States Patent [19]

Labrie

[11] Patent Number: 5,610,150

[45] Date of Patent: Mar. 11, 1997

[54] METHOD OF TREATMENT OF ANDROGEN-RELATED DISEASES

[75] Inventor: Fernand Labrie, Ste-Foy, Canada

[73] Assignee: Endorecherche Inc., Canada

[21] Appl. No.: 472,512

[22] Filed: Jun. 7, 1995

Related U.S. Application Data

[62] Division of Ser. No. 98,607, Sep. 10, 1993, which is a division of Ser. No. 963,278, Oct. 19, 1992, Pat. No. 5,372,996, which is a continuation of Ser. No. 376,710, Jul. 7, 1989, abandoned.

[51] Int. Cl.$^6$ .................................................. A01N 45/00
[52] U.S. Cl. ........................ 514/170; 514/171; 514/172; 514/177
[58] Field of Search ............................. 514/170, 15, 16, 514/17, 114, 117, 800, 169, 171; 540/4, 5, 22, 23; 522/304, 515, 522, 540

[56] References Cited

U.S. PATENT DOCUMENTS

| | | |
|---|---|---|
| 3,995,060 | 11/1976 | Neri et al. . |
| 4,024,248 | 5/1977 | Konig et al. . |
| 4,055,641 | 10/1977 | Benson et al. . |
| 4,087,461 | 5/1978 | Robinson ............................ 260/586 |
| 4,100,274 | 7/1978 | Dutta et al. . |
| 4,118,483 | 10/1978 | Konig et al. . |
| 4,139,638 | 2/1979 | Neri et al. . |
| 4,161,540 | 7/1979 | Neri et al. . |
| 4,191,759 | 3/1980 | Johnston et al. . |
| 4,235,893 | 11/1980 | Brodie . |
| 4,329,364 | 5/1982 | Neri et al. . |
| 4,386,080 | 5/1983 | Crossley et al. . |
| 4,472,382 | 9/1984 | Labrie et al. . |
| 4,481,190 | 11/1984 | Nestor et al. . |
| 4,547,493 | 10/1985 | Teutsch et al. . |
| 4,634,696 | 1/1987 | Teutsch et al. . |
| 4,659,516 | 4/1987 | Bowler et al. . |
| 4,659,695 | 4/1987 | Labrie . |
| 4,732,912 | 3/1988 | Pilgrim et al. . |
| 4,751,240 | 6/1988 | Bowler et al. . |
| 4,760,053 | 7/1988 | Labrie . |
| 4,760,061 | 7/1988 | Edwards et al. . |
| 4,775,661 | 10/1988 | Labrie . |
| 4,822,528 | 4/1989 | Columbo et al. . |
| 4,895,715 | 1/1990 | Neri ........................................... 424/10 |

(List continued on next page.)

FOREIGN PATENT DOCUMENTS

| | | |
|---|---|---|
| 1066988 | 7/1988 | Australia . |
| 1077888 | 8/1988 | Australia . |
| 3156989 | 9/1989 | Australia . |
| 058481 | 8/1982 | European Pat. Off. . |
| 138504 | 4/1985 | European Pat. Off. . |

(List continued on next page.)

OTHER PUBLICATIONS

Auchus Riess, et al., *Biochemistry*, 1986, 25, 7295–7300.
Beardwell, et al., *Cancer Chemo. Pharmacol.* (1983) vol. 10, No. 3 pp. 158–160.
Begin, et al., *Molecular and Cellular Endocrinology*, 58 (1988) 213–219.
Belis, et al., *J. Androl.*, 4, 144–149, 1983.

(List continued on next page.)

*Primary Examiner*—Charles T. Jordan
*Assistant Examiner*—Anthony R. Chi
*Attorney, Agent, or Firm*—Ostrolenk, Faber, Gerb & Soffen, LLP

[57] ABSTRACT

A method of treatment of androgen-related diseases such as prostate cancer in susceptible male animals, including humans, novel antiandrogens and/or novel sex steroid biosynthesis inhibitors as part of a combination therapy. Sex steroid biosynthesis inhibitors, especially those capable of inhibiting conversion of dehydroepiandrosterone (DHEA) or 4-androstenedione ($\Delta^4$-dione) to natural sex steroids (and testosterone into dihydrotestosterone) in peripheral tissues, are used in combination with antiandrogens usually after blockade of testicular hormonal secretions. Antiestrogens can also be part of the combination therapy. Pharmaceutical compositions and two, three, four and five component kits are useful for such combination treatment.

15 Claims, 1 Drawing Sheet

U.S. PATENT DOCUMENTS

| | | |
|---|---|---|
| 4,904,661 | 2/1990 | Pilgrim . |
| 5,021,414 | 6/1991 | Pilgrim et al. . |
| 5,023,234 | 6/1991 | Labrie . |
| 5,053,403 | 10/1981 | Orentreich et al. . |
| 5,064,813 | 11/1991 | Labrie . |
| 5,204,337 | 4/1993 | Labrie . |
| 5,364,847 | 11/1994 | Labrie et al. . |
| 5,372,996 | 12/1994 | Labrie . |
| 5,393,785 | 2/1995 | Labrie et al. . |

FOREIGN PATENT DOCUMENTS

| | | |
|---|---|---|
| 160508 | 11/1985 | European Pat. Off. . |
| 163416 | 12/1985 | European Pat. Off. . |
| 166509 | 1/1988 | European Pat. Off. . |
| 0285383 | 10/1988 | European Pat. Off. . |
| 2529969 | 1/1976 | Germany . |
| 3339295 | 5/1984 | Germany . |
| 83545 | 10/1981 | Luxembourg . |
| 137542 | 9/1967 | New Zealand . |
| 142112 | 6/1968 | New Zealand . |
| 123341 | 9/1970 | New Zealand . |
| 181107 | 11/1978 | New Zealand . |
| 182661 | 7/1979 | New Zealand . |
| 201536 | 8/1982 | New Zealand . |
| 206745 | 1/1984 | New Zealand . |
| 207413 | 11/1984 | New Zealand . |
| 213652 | 9/1985 | New Zealand . |
| 222883 | 12/1987 | New Zealand . |
| 208441 | 1/1988 | New Zealand . |
| 214798 | 9/1988 | New Zealand . |
| 214998 | 6/1989 | New Zealand . |
| 222103 | of 1989 | New Zealand . |
| 223262 | 8/1989 | New Zealand . |
| 8601105 | 2/1986 | WIPO . |
| 8705216 | 9/1987 | WIPO . |
| 9010462 | 9/1990 | WIPO . |
| 9100732 | 1/1991 | WIPO . |
| 9100731 | 1/1991 | WIPO . |

OTHER PUBLICATIONS

Bhatnager, et al., *Biol. Chem.*, 253, 811–815, 1978.

Brooks, et al., *Proc. Soc. Experimental Biology and Medicine,* 169, 67–73 (1982).

Brooks, et al., *Steroids* 47/1, Jan. 1986 (1–19).

Brooks, et al., *The Prostate,* vol. 3, No. 1 pp. 35–44 (1982).

Brooks, et al., *Endocrinology,* vol. 109, No. 3 (1981) pp. 830–836.

Bruchovsky, et al., *J. Biol. Chem.,* vol. 243, No. 8 (1968) pp. 2012–2021.

Bull, et al., *Chem. Soc. Chem. Commun.,* 1986, pp. 451–453.

Chan, et al., *Biochem and Biophys Res. Comm.,* 144, No. 1, 166–171 (1987).

Chang, et al., *Biochemistry,* 1982, 27, 4102–4109.

Chin, et al., *J. Biol. Chem.,* 250(19), 1975, pp. 7682–7686.

Chin, et al. *J. Biol. Chem.,* 255, 3660–3664, 1980.

Cooke, Jr., *Tetrahedron Letters,* 22, 1983–1986, 1973.

Corbin, et al., *J. Steroid Biochem.,* 20(6B) 1369, No. A9 (1984).

Coy, et al., *Endocrinology,* vol. 110 (1982) pp. 1445–1447.

Coy, et al., *J. Med. Chem.,* vol. 19, No. 3 (1976) pp. 423–425.

Debruyne, et al. (1988)*Bailliére's Clin. Oncol. Int'l Pract. and Res.,* pp. 559–570.

De Klerk, et al., *The Prostate,* vol. 7 (1985) pp. 1–12.

De Larminat, et al., *The Prostate,* vol. 5 (1984), pp. 123–140.

Donnelly, "Continuous Subcutaneous Administration of 'Zoladex' (ICI 118,630 – An LH–RH Analogue) to Patients with advanced Prostatic Cancer", ICI.

Doorenbos, et al., *J. Pharm. Sciences* 63(4), 1974, pp. 620–622.

Doorenbos, et al., *J. Pharm. Sciences* 62(4), 1973, pp. 638–640.

Doorenbos, et al., *J. Pharm. Sciences* 60(8), 1971, pp. 1234–1235.

Dutta, et al., *J. Med. Chem.,* 21, No. 10, 1018–1024 (1978).

Earnshaw, et al., *Clin. Invest.,* 21, 13–21 (1984).

Erchegyi, et al., *Biochem. and Biophys. Research Comm.,* 100, No. 3, 915–920 (1981).

Farnsworth, *Invest. Urology* 6(4) 423–427, 1969.

Faure, et al., *LHRH and Its Analogs,* pp. 337–349 (1984).

Fujimoto, *J. Pharm. Soc. Jap,* 87:270 (1967).

Furr, et al. *J. Endocr.,* 113, R7–R9, 1987.

Geller, et al., 71st Ann. Meet. Endo. Soc. (1989) No. 1640.

George, et al., "The Effect of A 5–$\alpha$–Reductase Inhibitor on Androgen Physiology in the Prepubertal Male Rat", 71st Ann. Endo. Soc. Mtg. No. 1165 (1989).

Gibson, et al., *Angew Chem. Int. Ed.* 7 (1968) No. 12, pp. 919–930.

Gohring, et al., (1989), World Patent Information, vol. 11, No. 1, pp. 5–10.

Gormley, et al., 71st Ann. Meet. Endo. Soc. (1989) No. 1225.

Green et al., Nature, 320(13) Mar. 1986, pp. 134–139.

Groom, et al., *Biochem J.,* vol. 122 (1971) pp. 125–126.

Grunwell, et al., Steroids, 27(6), 1976, pp. 759–771.

Gyorki, et al., J. Steroidal Biochem. 25(3), 355–358, 1986.

Habenicht, et al., The Prostate II, 313–326, 1987.

Imperato–McGinley, et al., "Comparison of Plasma and Urinary C19 and C21 5$\alpha$–Metabolites in Subjects Treated With the 5$\alpha$–Reductase Inhibitor MK906 and Male Pseudohermaphrodites with Inherited 5$\alpha$–Reductase Deficiency", 71st Ann. Endo. Soc. Mtg., No. 1639 (1989).

Jordan, et al., Endocrinology, 124 (4), 1989, pp. 1717–1726.

Junkmann, (1957) "Long–Acting Steroids In Reproduction", *Recent Progr. Horm. Res.,* 13:1389–1427, Academic Press, New York.

Kadohama, et al., *J. Natl. Cancer Inst.,* 74, No. 2, pp. 475–486 (1985).

Kerle, et al., *J. Steroid Biochem.* 20 (6B) 1395, No. A61 (1984).

Labrie et al., J. Steroid Biochem. 19(1) 999–1007, 1184.

Labrie, et al. 7th Int. Congress of Endo. 1984, p. 98.

Labrie, et al. *Endocrinology* 123: 1412–1417, 1988.

Labrie, et al., *Important Advances in Oncology,* Eds. V. T. De Vita, et al. J. B. Lippincott Company, Philadelphia, pp. 193–217, 1985.

Labrie, The Prostate, 4, 579–594, 1983.

Labrie, et al., *Genitourinary Cancer,* pp. 157–199 (1987).

Labrie, et al., *J. Steroid Biochem.,* 28, No. 4 (1987) pp. 379–384.

Lambert, et al., *Ann. Clin. Biochem.* (1986) vol. 23 pp. 225–229.

Lee et al., Steroids 22, 677–685, 1973.

Lee, et al., J. Androl. 2(6) 293–299, 1981.

Lefebrve et al. Prostate 1982, 3661, 569–570 (Chem. Ab., vol. 99, 1983, Abst. 188132r).

Levesque, et al., J. Med. Chem. 1991, 34 1624–1630.

Liang, et al., *Endocrinology,* vol. 112, No. 4, pp. 1460–1468 (1983).

Liang, et al., *The Journal of Biological Chemistry,* vol. 259, No. 2, pp. 734–739 (1984).
Lubahn et al. Proc. Natl Acad. Sci. USA 86, 9534–9538, Dec. 1989.
Lubahn et al., Science, 1988 pp. 327–330.
Luthy, et al., J. Steroidal Biochem. 31(5) 845–52, 1988.
Macaulay, et al., J. Steroidal Biochem. 26(5) 535–538, 1987.
McConnell, et al., *Journal of Urol.,* AUA 84th Ann. Meeting, 141, 239A, 280 (1989).
Mobbs, et al., J. Steroidal Biochem., 19(3), 1279–1290, 1983.
Mobbs, 71th An. Meeting of the Endocrine Soc., No. 1410, 1989.
Moore, et al., *J. Clin. Invest.,* vol. 63, pp. 351–357 (1979).
Musto, et al., Endo. Res. Comm. (1977), vol. 4, No. 2, pp. 147–157.
Nayfeh, et al., Steroids 14:3, 1969, pp. 269–283.
Neri et al, J. Steroidal Biochem., 1975(6), pp. 815–819.
Nestor, et al., *J. Steroid Biochem.,* 20 (6B), 1366, No. A3 (1984).
Nestor, et al., Contraceptive and Therapeutic Appl., pp. 3–10, 23–33, 1984.
Neumann, et al., *In: Clinics in Oncology,* vol. 1, pp. 41–64, 1982.
Petrow, et al., *J. Endo.,* 95, 311–313 (1982).
Plante, et al., *J. Steroid Biochem.,* 31(1), pp. 61–64 (1988).
Potts, et al., *Steroids* (1978) vol. 32, No. 2, pp. 257–267.
Poyet and Labrie, *Mol. Cell. Endocrinol.,* 42, 283–288, 1985.
Raucher, et al., J. Org. Chem., 1981, 46, 3558–3559.
Redding, Proc. Nat'l Acad. Sci. USA 80 1459–1452, 1984.
Riess, Institut de Chimie, Strasbourg, France (Jul. 31, 1964).
Rivier, et al., *J. Steroid Biochem.,* 20(6B), 1365, No. A1 (1984).
Rivier, et al., Contraceptive and Therapeutic Appl., pp. 11–22 (1984).
Robinson, et al., *J. Steroid Biochem.* 21, No. 5, 601–605 (1984).
Salman, et al., J. Steroid Biochem, vol. 33, No. 1, pp. 25–31, 1989.
Salman, et al., *J. Steroid Biochem.,* 26, 383–391, 1987.
Santen, LHRH and Its Analogues MTP Press, Lancaster England, pp. 351–364, 1984.

Schally et al., Cancer Treatment Reports, 68(1), 281–289.
Schwarz, Organic Synthesis Collective, vol. 3, pp. 332–333.
Séguin, et al. *Mol. Cell. Endocrinol.,* 21, 37–41, 1981.
Sharpless, et al., *Tetrahedron Letters,* 1979 (1973).
Simard, et al., *Mol. Cell. Endocrinol.,* 44, 261–270, 1986.
Simard, et al., *Mol. Endo.,* 2, No. 9, 775–784 (1988).
Solo, et al., Steroids, vol. 40, No. 6 (1982) pp. 603–614.
Stewart, et al., (1969) In: Solid Phase Peptide Synthesis, Freeman and Co., San Francisco.
Stoner (1989) The role of a 5α–reductase inhibitor in BPH. AUA Today, No. Nov./Dec.
Swaneck, et al., *Biochemical Biophysical Research Comm.,* 106, No. 4, pp. 1441–1447 (1982).
Taylor, *J. Endo.,* 113, 489–493 (1987).
Tenover, et al., "Effects of 24–Week Admin . . . ", 71st Ann. Mtg. Endo. Soc., No. 583 (1989).
Thomas, et al. *J. Biol. Chem.,* 258, 1587–1590, 11500 (1983).
Tobias, et al. *J. Biol. Chem.,* 257, 2783–2786, 1982.
Toomey, et al. (1989) 71st Ann. Meet. Endo. Soc. No. 1226.
Tora, et al. EMBO 8(7) 1981–1986, 1989.
Toth, et al. (1982) *J. Steroid Biochem* 17:653–660.
Voight et al., Endo 1973 92(4), pp. 1216–1222.
Wagner, et al., Acta. Endocrin. Suppl. 193, 52 (abst) (1975).
Wakeling, et al. *J. Endocr.,* 112, R7–R10, 1987.
Wakeling, et al. *J. Steroid Biochem.,* 30, 141–147. (1988).
Walsh, et al., *The Journal of Clinical Investigation,* vol. 57, Apr. 1976, pp. 1093–1097.
Wang, et al., Can J. Chem., 65, 2727, 1987.
Weinbauer, et al. (1986) *Acta Endocrinologica* 113:128–132.
Weiss, et al., Angew Chem. Int. Ed. 12 (1973) No. 10, p. 841.
Wenderoth, et al., *Endocrinology* vol. 113, No. 2, pp. 569–573 (1983).
Williams, et al., *Cancer Treatment Reports,* 71, No. 12, 1197–1201 (1987).
Wilson, *Endocrinology,* vol. V, Section 7, pp. 491–508 (1975).
Grant & Hackh's Chemical Dictionary (1987) p. 14.
Klingmueller, *J. Steroid Biochem.,* 20(6B) 1395 (1984).

METHOD OF TREATMENT OF ANDROGEN-RELATED DISEASES

RELATED APPLICATION

This is a division of application Ser. No. 08/098,607, filed Sep. 10, 1993, which is a division of application Ser. No. 07/963,278, filed Oct. 19, 1992, now U.S. Pat. No. 5,372,996 which is in turn a continuation of U.S. application Ser. No. 07/376,710, filed Jul. 7, 1989, now abandoned. Priority under 35 U.S.C. §120 is claimed as to all of the foregoing.

BACKGROUND OF THE INVENTION

This invention relates to a method of treatment of androgen-related diseases such as prostate cancer in warm-blooded male animals (including humans) in need of such treatment, and in particular, to a combination therapy comprising administering an antiandrogen in association with an inhibitor of sex steroid biosynthesis to such animals. The invention also includes pharmaceutical compositions and kits useful for such treatment. Androgen-dependent diseases include diseases whose onset, maintenance or progress is, at least in part, dependent upon biological activities induced by androgens (e.q. testosterone and dihydrotestosterone). In one embodiment, the invention provides a treatment of hormone-dependent prostate cancer in warm-blooded male animals which comprises administering both an antiandrogen and at least one inhibitor of sex steroid biosynthesis capable of inhibiting conversion of dehydroepiandrosterone or 4-androstenedione to natural sex steroids in extra-testicular and extra-adrenal tissues.

While various investigators have been studying hormone-dependent prostate cancer, none have proposed the combination therapy of this invention.

A. V. Schally et al., Cancer Treatment Reports, 68 (No. 1) 281–289 (1984), summarize the results of animal and clinical studies on growth inhibition of hormone-dependent mammary and prostate tumors by use of analogues of luteinizing hormone-releasing hormones, the so-called LHRH agonists and suggest that LHRH analogs and/or antagonists may have potential for treating breast cancer.

T. W. Redding and A. V. Schally, Proc. Natl Acad. Sci. UA 80, 1459–1462 (1983), relates to inhibition of prostate tumor growth in rats by chronic use of an LHRH agonist, [D-Trp$^6$] LHRH.

U.S. Pat. No. 4,329,364 relates to use of the antiandrogen, 4'-nitro-3'trifluoromethyl isobutyranilide for treatment of prostatic cancer.

U.S. Pat. No. 4,472,382 relates to treatment of prostate adenocarcinoma, benign prostate hypertrophy and hormone-dependent mammary tumors may with various LHRH agonists and treatment of prostate adenocarcinom and benign hypertrophy by use of various LHRH agonists and an antiandrogen.

U.S. Pat. No. 4,659,695 (Labrie) relates to treatment of prostate cancer in animals whose testicular hormonal secretions are blocked. The method of treatment includes administering an antiandrogen such as flutamide as an inhibitor of sex steroid biosynthesis such as aminoglutethimide and/or ketoconazole.

Some clinical improvement in men with prostate cancer by use of the two LHRH agonist, Buserelin and Leuprolide, is also reported by N. Faure et al. at pages 337–350 and by R. J. Santen et al. at pages 351–364, respectively, LHRH and its Analogues—A new Class of Contraceptive and therapeutic Agents (B. H. Vickery and J. J. Nestor, Jr., and E. S. E. Hafez, eds), Lancaster, MTP Press, (1984).

R. Santen et al., The Journal of Steroid Biochemistry, volume 20, no 6B, at page 1375 (1984), relates that the use of ketoconazo in combination with chronic administration of Leuprolide in rodents decreased basal and Leuprolide-stimulated testosterone levels.

One of Applicant's Co-pending U.S. patent applications Ser. No. 07/321,926 filed Mar. 10, 1989, relates to a combination therapy treatment of estrogen-related diseases by inhibiting ovarian hormonal secretions and administering an antiestrogen in combination with at least one of several enumerated activity blockers, sex steroid formation inhibitors and the like.

D. Kerle et al., The Journal of Steroid Biochemistry, volume 20, no. 6B, at page 1395 (1984) relates to the combined use of a LH analogue and ketoconazole producing objective responses in some prostate cancer patients who have relapsed or failed to respond to treatment with a LHRH analogue alone. that use of a combination therapy of an LHRH agonist (Buserelin) and an antiandrogen (Anandron) to treat advanced prostate cancer in previously untreated patients effects simultaneous elimination of androgens of both testicular and adrenal origin.

F. Labrie et al., J. Steroid Biochem., 19, 999–1007 (1983), disclose the treatment of prostate cancer by the combined administration of an LHRH agonist and an antiandrogen. Labrie et al. disclose animal and clinical data in support of the proposition that the combined LHRH/antiandrogen treatment neutralizes the stimulatory influence of all androgens on the development and growth of androgen-dependent prostatic cancer.

F. Labrie et al., Abstracts of the 7th International Congress Endocrinology, Excerpta Medica (1984) at page 98 disclose that treatment of prostate cancer patients with LHRH agonists alone causes a transient increase in serum androgen levels lasting for 5 to 15 days before castration levels are reached. While F. Labrie et al. recommend that orchiectomy, estrogen and LHRH agonists alone should not be further used for treatment of prostate cancer in the absence of a pure antiandrogen, there still is a need for a method of treatment of prostate cancer that effects more complete androgen blockage at the start as well as during the full period of treatment.

There are many data indicating that estrogens have a stimulatory effect on prostatic growth (Lee et al., 1981; J. Androl. 2: 293–299; Belis et al., 1983; J. Androl. 4: 144–149; Walsh and Wilson, 1976; J. Clin. Invest. 57: 1093–1097; De Klerk et al., 1985; Prostate 7, 1–12; Habesucht et al., 1987; Prostate 11: 313–326). Estrogens have also been found to enhance the growth-promoting effect of androgens (Farnsworth, 1969; Invest. Urol. 6: 423–427; Groom et al., 1971; Biochem. J. 122: 125–126; Lee et al., 1973; Steroids 22: 677–683).

Estrogen receptors have been demonstrated in human normal, hyperplastic Endocrine Soc., Meeting, abst. No. 1410; Mobbs et al., 1983; J. Steroid Biochem. 19, 1279–1290; Wagner et al., 1975; Acta Endocrinol. (Kbh), suppl. 193, 52; and also in laboratory animal prostatic tissue (Swaneck et al., 1982; Biochem. Biophys. Res. Commun. 106: 1441–1447).

Moreover, androgen receptor levels were found to be elevated in prostatic tissue of patients treated with estrogen, thus indicating a stimulatory effect of estrogen on the level of androgen receptors in prostatic tissue (Mobbs et al., 1983; J. Ster. Biochem. 19, 1279–1290). A similar stimulatory effect of estrogen has been observed in the dog prostate (Moore et al., 1979; J. Clin. Invest. 63, 351–357).

In the prostate as well as in many other tissues, testosterone is irreversibly converted by 5α-reductase into the more potent androgen dihydrotestosterone (Bruchovsky and Wilson, J. Biol. Chem. 243: 2012–2021, 1968; Wilson, Handbook of Physiology 5 (section 7), pp. 491–508, 1975). Inhibitors of 5α-reductase have been found to inhibit prostatic grow (Brooks et al., Endocrinology 109: 830, 1981; Brooks et al., Proc. Soc. Exp. Biol. Med. 169: 67, 1982; Brooks et al., Prostate 3: 35, 1982; Wenderoth et al., Endocrinology 113, 569–573, 1983; McConnell et al., J. Urol. 141: 239A, 1989); Stoner, E., Lecture on the role of 5α-reductase inhibitor in benign prostatic hypertrophy, 84th AUA Annual Meeting, Dallas, May 8th, 1989.

The inhibitory effect of the 5α-reductase inhibitor Merck L. 652,931 on prostatic and seminal vesicle development in the prepubertal rat was described in Proc. 71st Annual Meeting of Endocrine Society, abst. #1165, p. 314, 1989. The inhibitory effect of MK-906 on dihydrotestoster formation in men has been described in men by Gormley et al., in Proc. 71st Annual Meeting of Endocrine Society, abst. #1225, p. 329, 1989; Imperato-McGinley et al., in Proc. 71st Annual Meeting of Endocrine Society, abst. #1639, p. 432, 1989; Geller and Franson, in Proc. 71st Annual Meeting of Endocr. Soc., abst. #1640, p. 432, 1989, an Tenover et al., in Proc. 71st Annual Meeting of Endocr. Soc., abst. #583p. 169, 1989. The activity of the 5α-reductase inhibitors N,N-diethyl-4-methyl-3-oxo-4-aza-5α-androstane-17β-carboxamide (4-MA) and 6-methylene-4-pregnene-3,20-dione (LY207320) has been described by Toomey et al., Proc. 71st Annual Meeting of Endocr. Soc., abst. #1226, p. 329, 1989.

SUMMARY OF THE INVENTION

It is an object of the present invention to provide combination therapy for the treatment of prostate cancer wherein the treatment selectively inhibits the formation and/or action of hormones which would otherwise contribute to tumor growth.

It is another object of the invention to provide combination therapy having increased effectiveness in slowing or reversing tumor growth.

It is another object of the invention to provide therapy for treating prostate cancer having significantly reduced frequency of unwanted side effects.

It is a further object of the invention to provide kits having a plurality of active ingredients (with or without diluent or carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

In one aspect, the present invention provides a method for treating prostate cancer in humans or other warm-blooded animals in need of such treatment, said method comprising the steps of blocking androgen receptors by administering a therapeutically effective amount of an antiandrogen having as part of its molecular structure a substituted or unsubstituted androgenic nucleus of the formula:

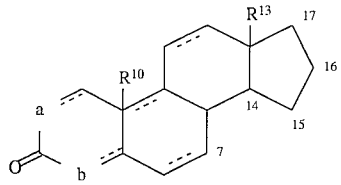

said antiandrogen having as another part of its molecular structure at least one side chain represented by the formula:

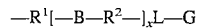

$$-R^1[-B-R^2-]_xL-G$$

wherein said side chain is substituted onto said androgenic nucleus at a position selected from the group consisting of 6α, 7α, 14α, 15α, 16α, 17α and 17β, and wherein:

x is an integer from 0 to 6, wherein at least one of L and G is a polar moiety distanced from said ring carbon by at least three intervening atoms, and wherein:

$R^1$ and $R^2$ are independently either absent or selected from the group consisting of straight- or branched-chain alkylene, straight- or branched chain alkynylene, straight- or branched-chain alkenylene, phenylene and fluoro-substituted analogs of the foregoing;

B is either absent or selected from the group consisting of —O—, —S—, —Se—, —SO—, —SO$_2$—, —NR$^3$—, —SiR$^3{}_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene (R$^3$ being hydrogen or lower alkyl);

L is either a moiety which together with G, forms a heterocyclic ring having at least one nitrogen atom or is selected from the group consisting of lower alkyl, —CONR$^4$—, —CSNR$^4$—, —NR$^5$CO—, —NR$^5$CS—, —NR$^5$CONR$^4$—NR$^6$ —NR$^5$C—NR$^4$—, —SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO— and —SO$_2$— (R$^4$ and R$^5$ being independently selected from the group consisting of hydrogen and lower alkyl; and R$^6$ being selected from the group consisting of hydrogen, nitrile and nitro); and G is either a moiety which together with L forms a heterocyclic ring having at least one nitrogen atom or is selected from the group consisting of hydrogen, lower alkyl, lower alkenyl, lower alkynyl, (C$_3$–C$_7$)cycloalkyl, bromo(lower)alkyl, chloro(lower)alkyl, fluoro(lower)alkyl, carboxy(lower)alkyl, (lower)alkoxycarbonyl(lower)alkyl, (C$_6$–C$_{10}$)aryl, (C$_7$–C$_{11}$)arylalkyl, di(lower)alkylamino(lower)alkyl, fluoro-substituted analogs of the foregoing, said method of treatment further comprising the step of inhibiting sex steroid formation by administering a therapeutically effective amount of at least one sex steroid formation inhibitor.

In another aspect, the present invention provides a method for treatment of prostate cancer in a human or other warm-blooded animal in need of such treatment, said method comprising the steps of inhibiting sex steroid formation by administering a therapeutically effect of amount of an inhibitor of sex steroid formation capable of blocking formation of natural sex steroids from dehydroepiandrosterone and from 4-androstenedione in peripheral tissues (extra-adrenal and extra-testicular), or an inhibitor of sex steroid formation having as part of its molecular structure a substituted or unsubstituted sex-steroid nucleus, and, as another part of its molecular structure at least one side chain of the formula

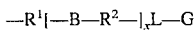

substituted onto a ring atom of said sex steroid nucleur wherein:

x is an integer from 0 to 6, wherein at least one of L and G is a polar moiety distanced from said ring carbon by at least three intervening atoms, and wherein:

$R^1$ and $R^2$ are independently either absent or selected from the group consisting of straight- or branched-chain alkylene, straight- or branched chain alkynylene, straight- or branched-chain alkenylene, phenylene and fluoro-substituted analogs of the foregoing;

B is either absent or selected from the group consisting of —O—, —S—, —Se—, —SO—, —SO$_2$—, —NR$^3$—, —SiR$^3{}_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene L is either a moiety which together with G, forms a heterocyclic ring having at least one nitrogen atom or is selected from the group consisting of lower alkyl, —CONR$^4$—, —CSNR$^4$—, —NR$^5$CO—, —NR$^5$CS—, —NR$^5$CONR$^4$—

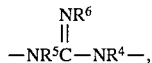

—SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO— and —SO$_2$— ($R^4$ and $R^5$ being independently selected from the group consisting of hydrogen and lower alkyl; and $R^6$ being selected from the group consisting of hydrogen, nitrile and nitro); and G is either a moiety which together with L forms a heterocyclic ring having at least one nitrogen atom or is selected from the group consisting of hydrogen, lower alkyl, lower alkenyl, lower alkynyl, ($C_3$–$C_7$)cycloalkyl, bromo(lower)alkyl, chloro(lower)alkyl, fluoro(lower)alkyl, cyano(lower)alkyl, carboxy(lower)alkyl, (lower)alkoxycarbonyl (lower) alkyl, ($C_6$–$C_{10}$)aryl, ($C_7$–$C_{10}$) arylalkyl, di(lower) alkylamino (lower)alkyl, fluoro-substituted analogs of the foregoing;

said method of treatment further comprising administering a therapeutical effective amount of an antiandrogen.

In another aspect, the present invention provides a method for treating prostate cancer in a human or other warm-blooded animal in need of such treatment, said method including the steps of administering a therapeutically effective amount of an inhibitor of 5α-reductase activity and administering a therapeutically effective amount of an antiandrogen.

In another aspect, the present invention provides a method for treating prostate cancer in a human or other warm-blooded animal in need of such treatment, said method including the steps of administering a therapeutically effective amount of an inhibitor of 17β-hydroxysteroid dehydrogenase and administering a therapeutically effective amount of an antiandrogen.

In another aspect, the present invention provides a method for treating prostate cancer in a human or other warm-blooded animal in need of such treatment, said method including the steps of administering an effective amount of an antiandrogen and at least one sex steroid formation inhibitor from the groups consisting of inhibitors of extragonadal and inhibitors of extraadrenal sex steroid formation.

The invention also provides kits or single packages combining two or more active ingredients useful in treating prostate cancer. A kit may provide (alone or in combination with a pharmaceutically acceptable diluent or carrier), an antiandrogen and at least one additional active ingredient (alone or in combination with diluent or carrier) selected from the group consisting of an LHRH agonist or LHRH antagonist, a sex steroid formation inhibitor (preferably an inhibitor of 5α-reductase activity an inhibitor of 17β-hydroxysteroid dehydrogenase activity or an inhibitor of 3β-hydroxysteroid dehydrogenase activity) and an antiestrogen.

The foregoing active ingredients may also be mixed in any of the foregoing combinations to form pharmaceutical compositions (with or without diluent or carrier) which, when administered, provide simultaneous administration of a combination of active ingredients resulting in the combination therapy of the invention. Preferably, when LHRH antagonist or agonist is used, it is administered parenterally. For this reason, it may be administered separately in instances where the other active ingredient are formulated for oral ingestion.

The term "sex steroid nucleus" includes estrogenic and androgenic nuclei.

As used herein, the term "androgenic nucleus" includes any compound which, in the absence of the side chain substituent specified herein ($R^1$[—B—$R^2$—]$_x$L—G), is capable of acting a an androgen as determined by a weight increase of at least 35 percent over a seven-day period of the ventral prostate of castrated rats treated with the compound in question (15 milligrams twice daily per 100 grams of body weight) versus a control group of castrated rats. Treatment should start on the day of castration. The precise test, other than any parameters set forth in this paragraph, is that reported in Labrie et al., J. Ster. Biochem. 28, 379–384, 1987.

As used herein, the term "estrogenic nucleus" includes any compound which, in the absence of the side chain substituent specified herein ($R^1$[—B—$R^2$—]$_x$L—G), is capable of acting a an estrogen as determined by a uterus of ovariectomized rats treated with the compound in question (0.5 mg twice daily per 100 grams of body weight) versus a control group of ovariectomized rats. Treatment should start on the day of castration. The precise test, other than any parameters set forth in this paragraph, is that reported in Simard et al., Mol. Endocrinol. 2: 775–784 (1988).

The following conventions apply to structural formulae set forth herein. Unless specifically designated to the contrary, substituents may have either α or β stereochemistry or, where valence permits, may represent one substituent in α position and another in β position. Presence of optional double bonds are independent of each other. All structures include salts thereof. Atoms of any sex steroid nucleus for which no substituent is shown or described may optionally be substituted or unsubstituted so long as such substitution does not prevent the nucleus from functioning as a "sex steroid nucleus" as defined herein. Those atoms having a defined substituent may optionally be further substituted by other substituents where their valence permits such further substitution. As used herein, the term "lower", when describing a chemical moiety means a moiety having 8 or fewer atoms. For instance, a "lower alkyl" means a $C_1$ to $C_8$ alkyl. Any moiety of more than two atoms may be straight- or branched-chain unless otherwise specified.

The term "sex steroid formation inhibitor" includes both androgen and estrogen formation inhibitors and encompasses any compound which inhibits the biosynthesis of active sex steroids or their precursors. One mechanism by which sex steroid formation inhibitors act is by blocking enzymes which catalyze production of natural sex steroids (e.g. dihydrotestosterone), 17β-estradiol and androst-5-ene-3β-17β-diol precursors to such sex steroids (e.g. androstenedione). Examples of such sex steroid formation inhibitors are compounds capable of blocking the enzymatic activity of, for example, 5α-reductase, 3β-hydroxysteroid dehydrogenase, 17β-hydroxysteroid dehydrogenase or aromatase.

DETAILED DESCRIPTION OF THE PREFERRED EMBODIMENTS

Figure 1:
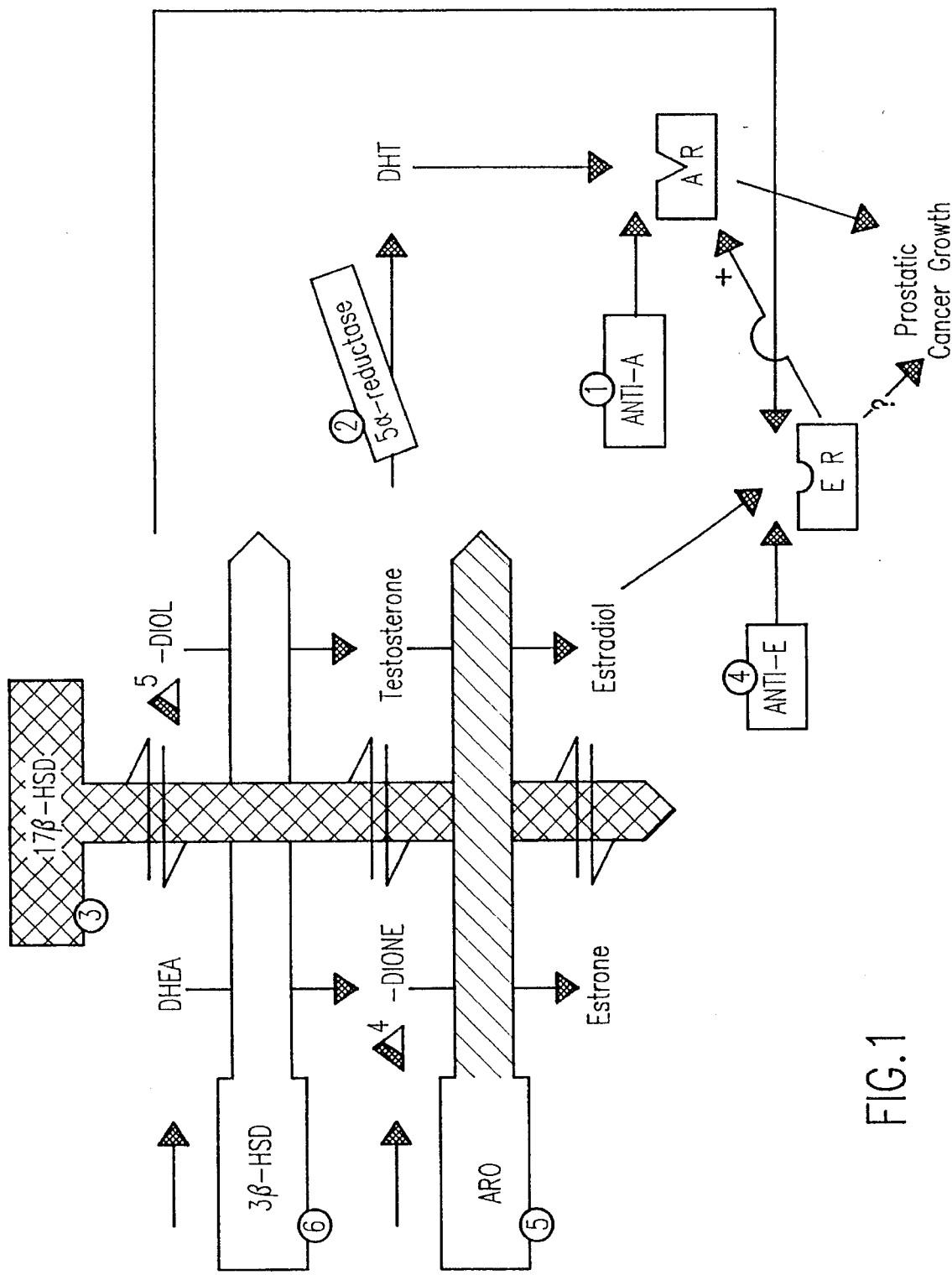

In a preferred aspect, a combination therapy for prostate cancer includes administering active ingredients effective to inhibit a variety of different mechanisms which may, directly or indirectly, lead to prostatic cancer growth. Desirably, the inhibition of biological activity which leads to prostatic cancer growth proceeds selectively, without substantially inhibiting other desirable biological activity. Side effects of the treatment are therefore minimized.

Activation of prostatic androgen receptors stimulates growth of prostatic cancer cells. Growth may be inhibited by blocking these receptors with antiandrogens as explained herein. Growth may also be inhibited by reducing the concentration of androgens available to activate the receptors by administering at least one sex steroid synthesis inhibitor. An inhibitor of 5α-reductase catalyzes conversion of testosterone to dihydrotestosterone (DHT). This is a particularly preferred sex steroid synthesis inhibitor because it selectively reduces DHT levels without reducing testosterone levels. DHT stimulates prostatic cancer growth to a much greater extent than does testosterone. Also absence of DHT forecloses fewer desirable biological functions than does absence of testosterone. For many patients, blocking of testosterone production is also appropriate.

It is believed that estrogens may also increase prostatic cancer growth. Without intending to be bound by theory, estrogens appear to at least be involved in increasing the number of androgen receptors, and may stimulate prostatic cancer growth directly by binding estrogen receptors. Regardless of the mechanism by which estrogens contribute to prostatic cancer growth, it has now been found that a combination therapy which includes inhibition of estrogen activity can enhance effectiveness of treatment without inhibiting desirable biological functions which, in males, are largely independent of estrogen.

There is shown in FIG. 1 a schematic representation of the site(s) of action of various drugs, enzymes and hormones. The following abbreviations are used: ER: estrogen receptor; AR: androgen receptor; DHEA: dehydroepiandrosterone; $\Delta^5$-diol: androst-5-ene-3 β, 17β-diol; $\Delta^4$-dione: androstenedione; DHT: dihydrotestosterone; Anti-A: antiandrogen; Anti-E antiestrogen; ARO: aromatase; 3β-HSD: 3β-hydroxysteroid dehydrogenase, $\Delta^5$-$\Delta^4$ isomerase; 17β-HSD: 17 β-hydroxysteroid dehydrogenase; 1: antiandrogen; 17β-hydroxysteroid dehydrogenase activity; 4: antiestrogen; 5; inhibitor of aromatase activity; 6: inhibitor of 3β-HSD activity.

Referring to FIG. 1, + means increase in androgen receptor levels. As may be seen from FIG. 1, stimulation of the androgen receptor is shown to stimulate prostatic cancer growth, and is therefore to be prevented. In addition, stimulation of the estrogen receptor leads to increased levels of androgen receptors and thus may, in addition, exert direct stimulatory effects on prostatic cancer growth. The action of estrogens is therefore to be prevented. Blockers of sex steroid formation from DHEA and $\Delta^4$-dione in peripheral tissues does not cause inhibition of adrenal glucocorticoid formation. For example, cortisol and aldosterone production is not inhibited and significant complications which could result from their inhibition are avoided. The desired inhibition of sex steroid formation is thus aimed selectively at androgens and estrogens.

A method of inhibiting activation of the androgen receptor is treatment with an effective antiandrogen compound having an affinity for the receptor site such that it binds to the receptor site and prevents androgens from binding and activating the site. It is important to select antiandrogens which tend to be pure antagonists and which have no agonistic activity. Otherwise, the antiandrogen which blocks the receptor site from androgens, may itself activate the site. Preferred antiandrogens are discussed in detail below. Because it is extremely difficult to block all receptor sites, it is desirable to simultaneously decrease the concentration of androgens available to activate androgen receptors in the prostatic cancer tissue. Hence, it is desirable to inhibit secretion of androgens by the testis. This may be accomplished by a variety of known techniques including but not limited to surgical orchiectomy or by administering LHRH agonists or antagonists. For example, LHRH analogues act in a manner effective to stop the production of bioactive luteinizing hormone, the hormone necessary to cause the testis to produce and secrete androgens and other hormones which may be converted to androgens in peripheral tissues. For some patients, it may be unnecessary to inhibit testicular hormonal secretions where sufficiently potent antiandrogens and sex steroid biosynthesis inhibitors are administered.

As may be seen from the scheme of FIG. 1, a number of hormones (especially DHEA and $\Delta^4$-dione) released by the adrenals may be converted by a variety of biological pathways into androgens and estrogens in peripheral tissues. The most potent androgen produced is DHT. It is therefore highly desirable to include an inhibitor of 5α-reductase which prevents the conversion of testosterone into the more potent androgen DHT.

In peripheral tissues, in addition to DHT, the precursors DHEA and $\Delta^4$-dione can be converted into the estrogens $\Delta^5$-diol and estradiol. It is desirable to have an inhibitor of 17β-hydroxysteroid dehydrogenase which prevents the formation of testosterone as well as of $\Delta^5$-diol and estradiol. In addition, since $\Delta^4$-androstenedione can be converted into estrone and then to estradiol, it may be useful to block the activity of aromatase, the enzyme responsible for such conversion. Other sex steroid formation inhibitors, such as inhibitors of 3β-HSD can also be used. However, as mentioned earlier, when 3β-HSD is blocked in peripheral tissues, it is also likely that a similar inhibition will take place in the adrenals, thus leading to low secretion of glucocorticoids and mineralocorticoids. When such compounds are used, essential glucocorticoids and sometimes mineralocorticoids should be added back as part of the therapy.

Estrogens, at physiological concentrations, are known to stimulate the growth of the human prostatic cancer cell line LNCaP. This effect of estrogen may be inhibited, however, by antiestrogenic compounds described herein.

In one embodiment, the present invention provides a method of treating prostate cancer comprising the step of administering a therapeutical effective amount of an antiandrogen, and of administering a therapeutically effective amount of an inhibitor of sex steroid formation which has, as part of its molecular structure, a substituted or unsubstituted estrogen nucleus of general structure I:

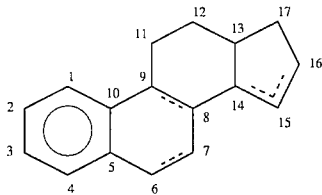

wherein the dotted lines represent optional pi bonds; and wherein said compound includes as another part of its molecular structure a side chain substitution onto a ring carbon of said general structure I in at least one position selected from the group consisting of 7, 14, 15, 16, 17 (preferably 7α, 15α, or 17α), said side chain being of the formula —R¹[—B—R²—] L—G, as defined above, wherein general structure I further includes at least one substitution selected from the group consisting of 15-halo, 16-halo, a 15,16 bridge atom (preferably carbon), a 14,15 bridge atom (preferably oxygen), and a 16-pi-bonded lower alkyl.

In certain embodiments, the antiandrogen utilized in the present invention may be represented by the general formula:

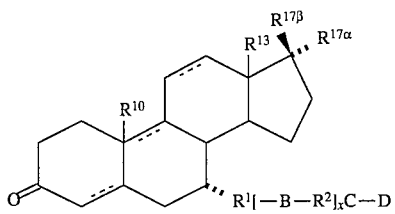

wherein the dotted lines represent optional double bonds; wherein $R^{10}$ is hydrogen or lower alkyl, $R^{13}$ is absent, hydrogen or methyl in β position, $R^{17(\alpha)}$ is selected from the group consisting of hydrogen, hydroxyl, lower alkanoyloxy, lower alkyl, lower alkenyl, lower alkynyl, halo(lower)alkyl, halo(lower)alkenyl, halo(lower)alkynyl and fluoro-substituted (β) aromatic ring, and a moiety which, together with $R^{17(\beta)}$ forms

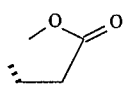 III $R^{17(\beta)}$ is selected from the group consisting of hydroxyl, ($C_1$-$C_{20}$) alkanoyloxy, ($C_3$-$C_7$)alkenoyloxy, ($C_3$-$C_7$)alkynoyloxy, aroyloxy, alkenoyloxy, cycloalkenyloxy, 1-alkyloxy-alkyloxy, 1-alkyloxycycloalkyloxy, alkylsilyloxy, carboxyl, alkanoyl and a moiety which together with $R^{17(\alpha)}$ forms

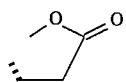 III

Antiandrogens useful in the combination therapy of the invention also include but are not limited to flutamide (available from Schering-Plough Corp., Kenilworth, N.J., under trade name EULEXIN), Nilutamide (available from Roussel of Paris, France, under trade name ANANDRON), cyproterone acetate (available from Schering AG, Berlin under trade name ANDROCUR), Casodex available from ICI Pharmaceuticals, Macclesfield, England. Preferably, the antiandrogen has, as part of its molecular structure, a substituted or unsubstituted androgenic nucleus, and as another part of its molecular structure, the side-chain —R'[—B—R²—]$_x$ L—G as defined above. Numerous syntheses of the preferred compounds set forth in the U.S. patent application of Labrie and Mérand entitled "Androgen Derivatives for use in the inhibition of sex steroid activity" which is being executed on even date herewith, the entire disclosure of which is hereby incorporated by reference as though fully set forth herein. A preferred antiandrogen is

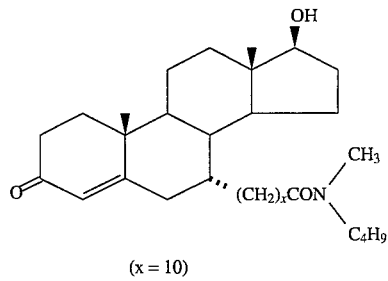

(x = 10)

which may be synthesized as set forth below.

EXAMPLE 1

Synthesis of N-butyl, N-methyl-11-(17'β-hydroxy- 4'-androsten-3'-on-7'α-yl) undecanamide (EM 101) (5, x=10) (Scheme 1)

17β-acetoxy-7α-(11'-hydroxy undecanyl)- 4-androsten-3-one (2)

Under argon atmosphere, in a flame dried apparatus with magnetic stirrer, a solution of 11-bromo undecanol tetrahydropyranyl ether (25 g, 74 mmol) in anhydrous THF (150 ml) was added dropwise to iodine-activated magnesium (1.9 g). The mixture was kept at room temperature overnight a then was cooled to –30° C. and anhydrous cuprous chloride (0.3 g) was added quickly. After 45 min of stirring at this temperature, commercial 4,6-androstadien-17β-ol-3-one acetate (1) (10 g, 30.5 mmol) in anhydrous THF (100 ml) was added dropwise during 4 h. After 35 min, acetic acid (6 ml) and water (100 ml) was added. The mixture was allowed to reach room temperature and was stirred overnight. Afterwards, the organic compound was extracted with ether (3×). The organic layers were washed with water, dried on magnesium sulfate and evaporated. The residue was dissolved in acetic acid (35 ml) and water (100 ml) and kept 48 h at room temperature. And then, the organic compounds were extracted with ether (3×). The organic layers were washed with saturated sodium bicarbonate solution and water, dried on magnesium sulfate and evaporated. The product was purified by Silica gel dry column chromatography (Kieselgel, 60F254, Merk, 0.063–0.200 mm, 150 g). Elution with a mixture of methylene chloride and ethyl acetate (20:1 v/v) gave 17β-acetoxy-7α-( 11'-hydroxy-undecanyl)-4-androsten-3-one (2a, 1.46 g, 2.8 mmol, 9.2%) as a colorless oil; IR $v_{max}$ neat 3450, 1740, 1685, 1620 and 1245 cm$^{-1}$; NMR 0.84 (s, 3H, 18'—CH₃), 1.21 (s, 3H, 19'—CH ₃), 2.05 (s,3H, OCOCH₃), 3.61 (t, 2H, J=6.59 Hz, H—C.1'), 4.61 (t, 1H, J= 7.69 Hz, H—C.17) and 5.73 (s, 1H, H—C.4) and 17β-acetoxy-7β-(11' -hydroxy undecanyl)-4-androsten-3-one (2b, 0.9 g, 1.7 mmol, 5.6%) as a colorless oil.

11-(17'β-acetoxy-4'-androsten-3'-on- 7'α-yl) undecanoic acid (3)

To 17β-acetoxy-7α-(11'-hydroxy undecanyl)- 4-androsten-3-one (2a, 800 mg, 1.6 mmol) dissolved in acetone (50 ml) and cooled to 0° C. was added under stirring during 5 min, a solution of Jones' reagent ( 8N chromic acid solution) (0.283 ml). After 15 min, isopropanol ( 0.5 ml) was added followed by water and the mixture was extracted with ethyl acetate (3×). The organic layers were washed with brine, dried on magnesium sulfate and evaporated to dryness under reduced pressure. The crude 11-(17'β-acetoxy-4'-androsten-3'-on-7 'α-yl) undecanoic acid (3) (740 mg) was used in the next step without purification.

N-butyl, N-methyl-11-(17'β-acetoxy-4' -androsten-3'-on-7'α-yl) undecanamide (4)

To a solution of the above undecanoic acid derivative 3 (390 m 0.78 mmol) in anhydrous methylene chloride (8 ml) cooled at −10° C. was added, under stirring, triisobutylamine (240 μl) and isobutylchloroformate (140 μl). After 30 min, N-methylbutylamine (1.8 ml) was added and was added. The organic solution was washed with 1N hydrochloric acid, water, saturated sodium bicarbonate solution and finally with water, dried on magnesium sulfate and evaporated to dryness. The residue was chromatographed on silica gel (Kieselgel, 60F254, Merck, 0.063–0.200 mm, 20 g). Elution with a mixture of diethyl ether and methylene chloride (1:20, v/v) gave N-butyl, N-methyl-11-(17'β-acetoxy- 4'-androsten-3'-on-7'α-yl) undecanamide 4 (230 mg, 0.39 mmol, 46% for the alcohol 1640 and 1240 (2a) as a colorless oil; IR $v_{max}$ neat 1740, 1680, and 1240 cm$^{-1}$; NMR 0.84 (s, 3H, 18'-CH$_3$), 0.95 (t, 3H, J=6.93 Hz, N—(CH$_2$) $_3$CH$_3$), 1.21 (s, 3H, 19'-CH$_3$), 2.04 (s, 3H, OCOCH$_3$), 2.91 and 2.97 (2s, 3H, N—CH$_3$), 3.26 and 3.36 (2t, 2H, J=7.86 Hz, N—CH$_2$C$_3$H$_7$), 4.61 (t, 1H, J=8.42 Hz, H—C.17') and 5.72 (s, 1H, H—C.4').

N-butyl, N-methyl-11-(17'β-hydroxy-4' -androsten-3'-on-7'α-yl) undecanamide (5) (EM 101)

The above acetoxy amide 4 (170 mg, 0.29 mmol) was dissolved in methanol (20 ml) and 6% potassium carbonate (2 ml) and heat at 65° C. for 200 min. After cooling, acetic acid (1 ml) and water (150 ml) were added and the mixture was extracted with ethyl acetate (3×). The organic layers were washed with water, dried on magnesium sulfate and evaporated to dryness. The residue was purified by Silica gel dry column chromatography (Kieselgel, 60F254, Merk, 0.063–0.200 mm, 20 g). Elution with a mixture of diethyl ether and methylene chloride (1:9, v/v) gave N-butyl-N-methyl-11-(17'β-hydroxy-4'-androsten-3'-on-7'α-yl) undecanamide (EM 101, 94 mg, 0.17 mmol, 58%) as a colorless oil; IR $v_{max}$ (neat) 3400, 1670 and 1640 cm$^{-1}$; NMR 0.80 (s, 3H, 18'-CH$_3$), 0.95 (t,3H, J=6.75 Hz, N—(CH$_2$) $_3$CH$_3$), 1.21 (s, 3H, 19'-CH$_3$), 2.91 and 2.97 (2s, 3H, N—CH$_3$), 3.25 and 3.35 (2t, 2H, J=7.3 Hz, N—CH$_2$C$_3$H$_7$), 3.67 (t, 1H, J=8.18, H—C.17') and 5.72 (s 1H, H—C.4').

SCHEME I

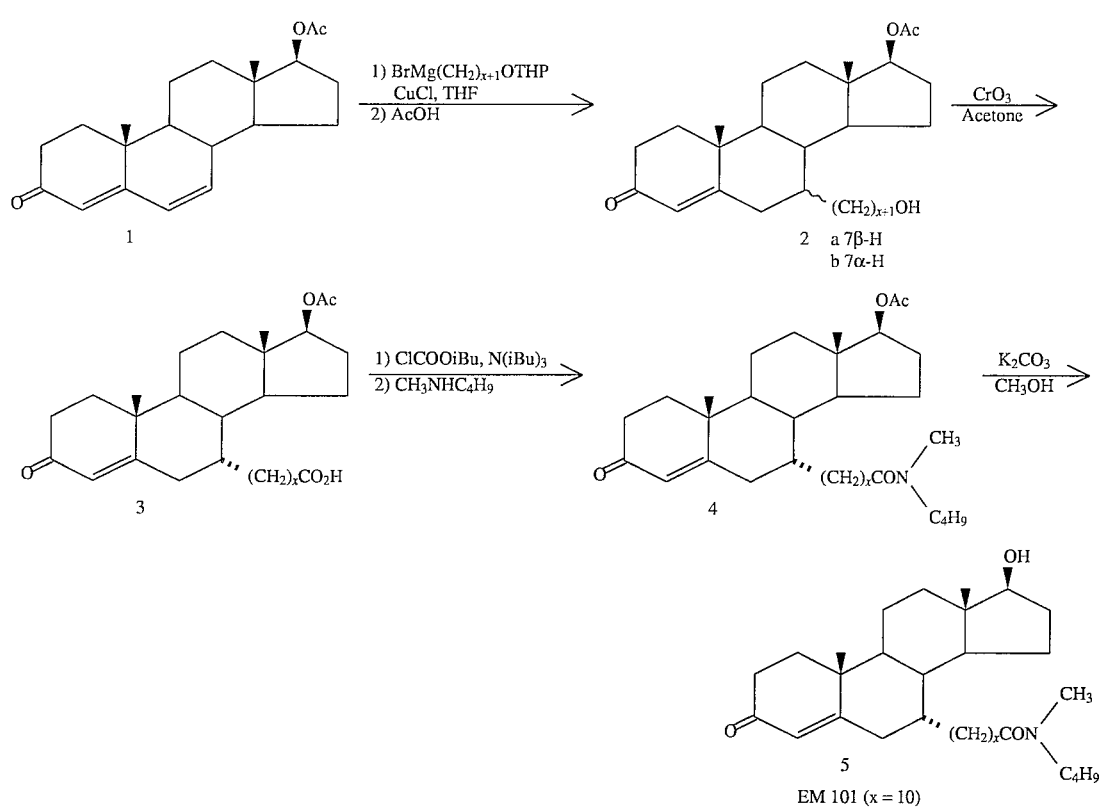

EM 101 (x = 10)

Sex steroid formation inhibitors useful in the combination therapy of the invention include but are not limited to inhibitors of 5 α-reductase activity, inhibitors of 17β-hydroxysteroid dehydrogenase activity, inhibitors of 3β-hydroxysteroid dehydrogenase activity and inhibitor of aromatase activity.

A typically suitable 5α-reductase inhibitor is MK-906, a product of Merck, Sharp & Dohme (Mc Connell et al., J. Urol. 141: 239A, 1989 Another inhibitor of 5α-reductase is 17β -N,N-diethylcarbamoyl-4-methyl-4-aza-5α-androstan-3-one (4-MA) (Brooks et al., Endocrinology 109: 830, 1981; Liang et al., Endocrinology 112: 1460, 1983). Other 4-azasteroids acting as 5α-reductase inhibitors can be formed in Liang et al., J. Biol. Chem. 259: 734–739, 1984; and in Brooks et al., Steroids 47: 1–19, 1986, 6-methylene-4-pregnene-3,20-dione has also been described as 5α-reductase inhibitor (Petrow et al., J. Endocrinol. 95: 311–313, 1982). Similar properties have been described for 4-methyl-3-oxo-4-aza-5α-pregnane-30(s)

Trilostane and epostane have been described as inhibitors of 3β-hydroxysteroid dehydrogenase activity (Ernshaw et al., Clin. Endocrinol. 21, 13–21, 1984; Robinson et al., J. Steroid Biochem. 21, 601–605, 1984; Lambert et al., Ann. Clin. Biochem. 23, 225–229, 1986; Potts et al., Steroids 32, 257–267, 1978) and have been successfully used for the treatment of breast cancer in combination with corticosteroids (Beardwell et al., Cancer Chemother. Pharmacol. 10: 158–160, 1983; Williams et al. Cancer Treat. Rep. 71, 1197–1201, 1987).

4-MA, (17β-N,N-diethylcarbamoyl-4-methyl-4-aza-5α-androstan-3-one) has been found to inhibit 3β-hydroxysteroid dehydrogenase activity in granulosa cells (Chan et al., Biochem. Biophys. Res. Commun. 144, 166–171, 1987). Epostane has been shown to inhibit 3β-hydroxysteroid dehydrogenase activity in pregnant goats (Taylor, J. Endocrinol. 113, 489–493, 1987).

Preferred inhibitors of 17β-hydroxysteroid dehydrogenase activity include but are not limited to:

N-butyl, N-methyl-11-(16'α-chloro-3',17' β-dihydroxy estra-1',3',5'(10')trien-7' α-yl) undecanamide ("EM 139").

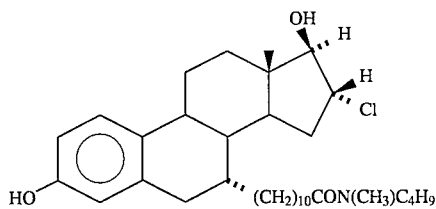

N-n-butyl-N-methyl-11-(16'α-chloro-3',17' α-dihydroxy-estra-1',3',5'(10')trien-7' α-yl) undecanamide ("EM 170")

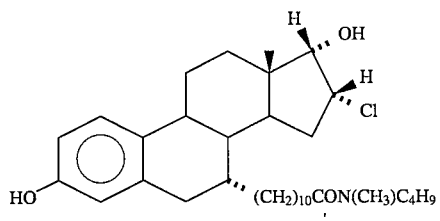

N-n-butyl-N-methyl-11-(16'α-bromo-3',17' α-dihydroxy-estra-1',3',5'(10')trien-7' α-yl) undecanamide ("EM 171")

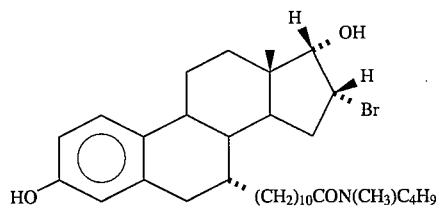

Examples of certain synthesis schemes for EM 139, EM 170 and E 171 are skill in the art will recognize analogous schemes for synthesizing analogous compounds.

EXAMPLE 2

SYNTHESIS OF PREFERRED SEX STEROID ACTIVITY INHIBITORS

Synthesis of a starting compound, N-n-butyl, N-methyl-11-(3'-benzoyloxy- 17'-oxo-estra-1',3',5'(10')-trien- 7'α-yl)undecanamide (14a) (SCHEME 2)

19-nor-testosterone acetate 3-enolacetate (7)

In an apparatus supplied with a drierite drying tube, a solution of 19-nor-testosterone (6) (100 g; 0.365 mole) in acetic anhydride (200 ml), pyridine (32 ml) and acetylchloride (320 ml) was heated at reflux under magnetic stirring, for 3 h and then concentrated to dryness under vacuum. The dry residue was triturated in absolute ethanol, filtered and washed with little portions of absolute ethanol. After drying, 19-nor-testosterone acetate 3-enolacetate was obtained as a white powder (121.4 g, yield 93%) mp. 176°–177° C. The structure was confirmed by spectroscopic means.

17β-acetoxy-estra-4,6-dien-3-one (8)

To a cooled suspension of enolacetate (121 g; 0.337 mole) in a mixture of DMF (330 ml) and water (7.2 ml) at 0° C. was added, under nitrogen, over a period of 1 h, N-bromosuccinimide (63 g). The resulting solution was stirred for an additional 0.5 h at 0° C. Then lithium carbonate (60.8 g) and lithium bromide (30.4 g) were added. The mixture was heated at 95° C. for 3 h and then poured into 1.7 l of ice-cold water containing 165 ml of glacial acetic acid. After stirring during 15 hours, the crude washed with water, dried in a desiccating apparatus and recrystallized twice from isopropyl ether (72 g, yield 68%, mp 110° C.). The structure was confirmed by spectroscopic means.

7α-(11'-acetoxy-undecyl) 17β-acetoxy estra- 4-en-3-one (9)

A. Preparation of reagents and solvents 11-bromo undecanol tetrahydro pyranyl ether 11-bromo-undecanol (100 g, 398 mmol) was dissolved in dry ether (768 ml) and the solution was cooled to 0° C. using an ice/H$_2$O bath. To this solution was added HCl gas (2.13 g, 58.4 mmol, 26 ml of HCl/ether).

To this mixture, a solution of 3,4-dihydro-2H-pyran (39.9 g, 43.3 ml) freshly distilled in dry ether (218 ml) was added over a period of 90 min. The solution was then stirred over a period of 16 hours at room temperature. Afterwards, sodium bicarbonate was added to the mixture. The residue was filtered and the solvent was evaporated under vacuum.

The product was then filtered through basic alumina (250 g, Woelm, grade II) using petroleum ether (30–60) as solvent (112 g, 81%).

B. Grignard reagent

In a dry three-neck flask (1000 ml) under dry argon, magnesium (12.0 g, 494 mmol) was placed and activated with iodine. Magnesium was heated with the flame to remove iodine and to dry the apparatus. The system was then cooled to −20° C., and a solution of 11-bromo-undecanol tetrahydro pyranyl ether (73.8 g, 211 mmol) in dry THF (420 ml) was added dropwise. The mixture was stirred under dry argon during one day at −20° C.

The mixture was cooled to −35° C. (±2° C.) using a dry ice/CCL$_4$/acetone bath. The anhydrous cuprous chloride (1.18 g, 12 mmol) was added and the C. Addition of Grignard reagent After 0.5 h, using the same apparatus mentioned above (Ar, − 35° C.), a solution of 17 β-acetoxy estra-4,6-diene-3-one (8) (32.0 g, 102 mmol) in dry THF (300 ml) was added dropwise over a period of 6 h to the Grignard reagent (red coloration appeared and disappeared). The mixture was stirred for an additional 1 h and, after removal the cooling bath, acidified (about 0° C.) with acetic acid (40 ml), diluted with water and extracted with ether (3×). The ether solution was washed with a saturated sodium bicarbonate solution and water. The organic layer was dried over anhydrous magnesium sulfate and evaporated under reduced pressure to dryness.

The residue was dissolved in MeOH (660 ml) and 5N HCl (180 ml), refluxed for 1 h and 45 min, then concentrated under reduced pressure and cooled in an ice bath. The mixture was then filtered to remove the white precipitate. After the solution had been diluted with water and extracted with methylene chloride (3×), the organic layer was dried over anhydrous MgSO$_4$ and evaporated under reduced pressure to dryness. Finally, the product (55.9 g, brown oil) was chromatographed on silica gel (Kieselgel 60F254, Merck, 0.063–0.200 mm, 1500 g). Elution with mixtures of methylene chloride and ethyl acetate (4:1 to 1:2 v/v) and then pure ethyl acetate gave crude 7α-(11'-hydroxy-undecyl)-17β-hydroxy estra-4-en-3-one (34.8 g) which was dissolved in dry pyridine (200 ml) and dry acetic anhydrid (200 ml), stirred 17 h at room temperature and then poured in icewater. The product was extracted with methylene chloride (3×), washed with 1N hydrochloric acid, water, saturated sodium bicarbonate and water (3× dried on anhydrous magnesium sulfate and filtered. After evaporation of solvent, the mixture (35 g) of 7α- and 7β -diacetoxyenones and degradation products of Grignard reagent were separated by flash chromatography on silica gel (Kieselgel 60, Merck, 230 mesh ASTM, 2.0 developed with a mixture of hexane and diethyl ether (2:3 v/v). The first product eluted was pure amorphous 7α-(11'-acetoxy undecyl) 17β-acetoxy-estra-4-en-3-one, (9) (20.8 g, 39.4 mmol, yield from dienone was 39.0%) Further elution gave the 7 β-isomer (10) (5.4 g, 10.3 mmol, 10%). All structures were determined by spectroscopic means.

7α-(11'-hydroxy-undecyl) estra-1,3,5( 10)-trien-3,17β-diol (11a)

Under dry argon, a solution of 7α-(11'-acetoxy undecyl) 17β-acetoxy-estra-4-en-3-one (9) (17.0 g, 32.4 mmol) in dry acetonitrile (150 ml) was added rapidly to a suspension of cupric bromide (14.8 g, 66.2 mmol) and mmol) and lithium bromide (2.89 g, 33.6 mmol) in warm acetonitrile (75 ml). The mixture was heated to reflux over a period of 30 min and stirred vigorously, and then cooled to room temperature. A saturated aqueous solution of sodium bicarbonate (50 ml) was added, and then the organic compound was extracted with ethyl acetate (3×150 ml). The organic layers were washed with water, dried over anhydrous magnesium sulfate, filtered and evaporated under vacuum to dryness. The residue was chromatographed on silica gel (Kieselgel 60F254 Merck 0.063– 0.200 mm; 1000 g). Elution with hexane-ethyl acetate (1:1 v/v) gave the 7α-(11'-acetoxy-undecyl) estra-1',3',5'(10')-trien-3,17β-diol, 17β-acetate (11b) (8.51 g; 50.3%) and the starting product (1.33 15%).

The above diacetate phenol (8.51 g, 16.2 mmol) was dissolved in methanol (90 ml) and sodium hydroxyde 30% (w/v) (9 ml). The mixture refluxed for 90 min under dry nitrogen. The solution was then concentrated under vacuum and diluted with hydrochloric acid (10% v/v). The mixture was extracted using ethyl acetate (4×150 ml) and the ethyl acetate extract was washed with water, dried over anhydrous magnesium sulfate, filtered and evaporated under vacuum. The evaporation gave 7α-( 11'-hydroxy undecyl) estra-1,3,5(10)-trien-3,17β-diol (11a) (6.99 g, 98% brut) as a yellow foam, the structure of which was confirmed by spectroscopic means.

3-benzoyloxy 7α-(11'-hydroxy undecyl) estra- 1,3,5(10)-trien-17β-ol (12)

The above triol (6.99 g; 15.8 mmol) was dissolved in acetone (25 ml) and an aqueous solution of sodium hydroxyde (1N, 19.1 ml). The mixture was cooled to 0° C. using an ice/water bath. Benzoyl chloride ( 2.22 ml, 19.1 mmol) was then added dropwise. The mixture was stirred for 40 min at 0° C. and then diluted with water. The solution was extracted using ethyl acetate (3×) and the organic layers were washed with a saturated aqueous solution of sodium bicarbonate and finally with water. The ethyl acetate solution was dried over anhydrous magnesium sulfate, filtered and evaporated under vacuum to dryness. Then, the residue was immediately chromatographed on silica gel (Kieselgel, 60F254, 0.063–0.200 mm; 500 g) The chromatography was carried out, first, using methylene chloride as solvent (about 1 liter) and secondly the pure 3-benzoyloxy 7α( 11'-hydroxy undecyl) estra-1,3,5(10)-trien-17β-ol (12), colorless 75%) was eluted with methylene chloride-ethyl acetate (5:1 about 1 liter and 4:1; v/v). The structure was confirmed by spectroscopic means.

11-(3'-benzoyloxy-17'-oxo-estra- 1',3',5'(10')-trien-7'α-yl) undecanoic acid (13)

To a cooled solution of 3-benzoyloxy-7α-(11'-hydroxy undecyl)estra-1,3,5 (10)-trien-17β-ol (12) (4.3 g) in acetone (100 ml) was added dropwise Jone's reagent (8N-chromic acid solution, 6.7 ml). Aft 30 min, isopropanol (40 ml) was added and the mixture was concentrated under vacuo. Water was added and the mixture was extracted four times with ethyl acetate. The organic layers were washed twice with brine, dried over magnesium sulfate and evaporated to dryness. The crude 11-( 3'-benzoyloxy- 17'-oxo-estra-1',3', 5'(10')-trien- 7'α-yl) undecanoic acid (13) (3.94 g) was used in the next step without purification.

Scheme 2

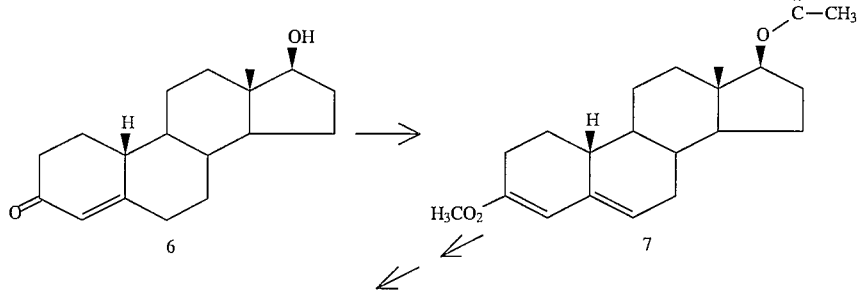

-continued
Scheme 2

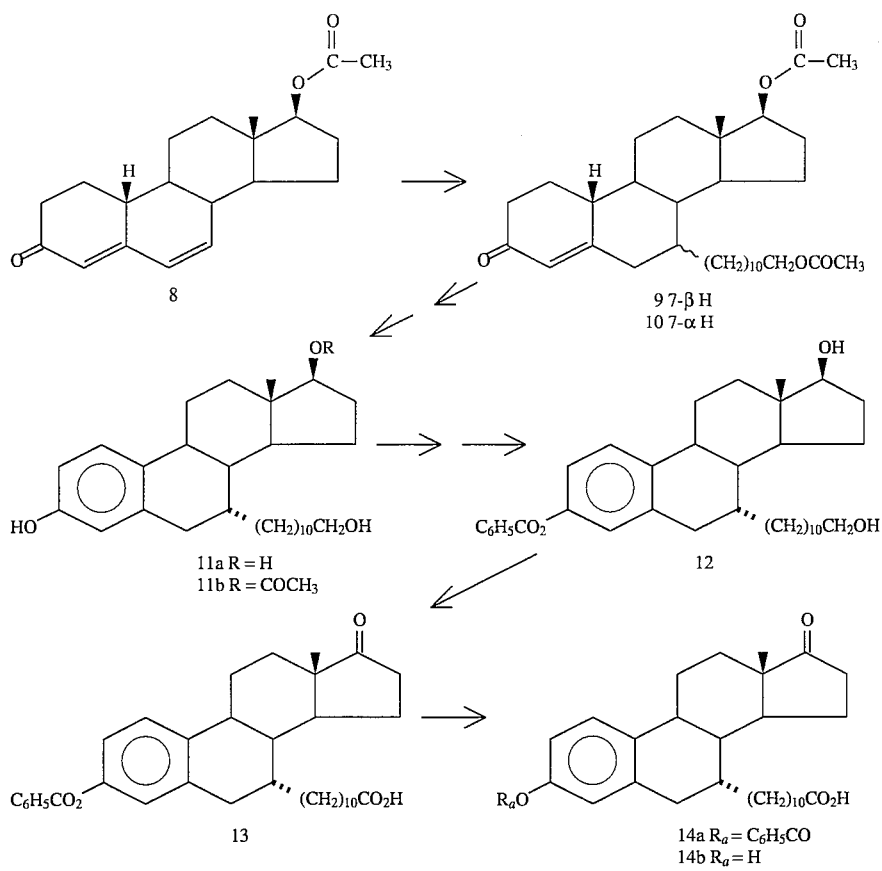

N-n-butyl,n-methyl-11-(3'-hydroxy-17' -oxo-estra-1',3',5'(10')-trien-7'α-yl ) undecanamide (14b)

To 11-(3'-benzoyloxy-17'-oxo-estra- 1',3',5'(10')-trien-7'α-yl) undecanoic acid (13) (3.94 g, 7.22 mmol), dissolved in anhydrous $CH_2Cl_2$ (100 ml) and cooled at $-10°$ C. was added tributylamine (2.18 ml, 9.15 mmol) and isobutylchloroformate (1.30 ml, 10.0 mmol). The solution was stirred during 35 min. and N-methylbutylamine (13 ml, 109.7 mmol) was added. The mixture was warmed to room temperature and stirred during 1 h. Afterward, $CH_2Cl_2$ was added and the organic phase was washed with 1N HCl, water, saturated sodium bicarbonated solution and finally with water, dried with anhydrous $MgSO_4$ and the solvent was removed under reduce pressure. The residue was purified by chromatography on silica gel. Elution with mixture of EtOAc/hexane (1.5:8.5 v/v) yielded N-butyl, N-methyl-11-( 3'-benzoyloxy-17'-oxo-estra-1',3',5'( 10')-trien-7'α-yl) undecanamide (14a) (4.25 g, 96%) as colorless oil; IR v (neat) 1750, 1725 and 1640 $cm^{-1}$. The above described benzoyloxy amide (341 mg, 0.54 mmol) was dissolve in methanol (10 ml) and cooled at 0° C. Following this 2N NaOH (5 ml) was added and the mixture was stirred during 60 min. at 0° C. The solution was neutralized with 1N HCl and extracted with $CH_2Cl_2$. The organic phase was dried with anhydrous $MgSO_4$ and the solvent was removed under reduced pressure. The residue was purified by chromatography on silica gel. Elution with mixture of EtOAc/hexane (3:7 v/v) yielded N-butyl, N-methyl-11-(3'-hydroxy-17'-oxo-estra- 1',3',4'(10)-trien-7'α-yl) undecanamide (14b) (284 mg, 97%) as colorless oil; $^1$H-NMR δ $(CDCl_3)$ 0.91 (s,3H,18'-$CH_3$), 2.76 app(d,1HJ= 16,3 Hz, part of ABX system, 6'-H) 2.96 and 2.98 (2s,3H N—$CH_3$), 3.27 and 3.38 $(2t_{app},2H,J=7.5$ Hz,N—$CH_2$—), 6.63 (broad s,1H,4'-H), 6.70 (broad d,1H,J= 8.5 Hz,2'-H), 7.12 (d,1H,J=8.4 Hz,1'-H); IR $v_{max}$ (neat) 3270, 1730, 1615 $cm^{-1}$; MS m/e 523 $(M^+,100\%)$, 508 $(M^+-CH_3,32\%)$, 142 $(C_2H_4CON(CH_3)C_4H_9^+$, 47%).

16-HALO-ESTRADIOL UNDECANAMIDE (SCHEME 3)
N-n-butyl, N-methyl-11-(3',17'-diacetoxy-estra- 1',3',5'(10'), 16'-tetraen-7'α-yl) undecanamide (15) The ketone amide 14b (163 mg, 0.50 mmol) was dissolved in isoprenyl acetate (10 ml). p-toluenesulfonic acid (44 mg) was the added and the solution was distilled to about two-thirds of the original volume in 7 h and was then stirred at reflux for 12 h. Afterwards, the solution was cooled with an ice-water bath and extracted with 50 ml of cooled ether. The ether was washed with a cooled saturated sodium bicarbonate and water. The organic phase was dried with anhydrous $MgSO_4$ and the solvent was removed under reduced pressure. The residue was filtered through alumina (15 mm×50 mm alumina Woehlm neutral, activity II) using a mixture of benzene-diethyl ether (3:7 v/v) as eluant. The solvent was removed under reduced pressure and, the residue was purified by flash chromatography on silica gel. Elution with mixture of EtOAc/hexane (1:4 v/v) yielded the N-butyl, N-methyl-11-(3',17'-diacetoxy-estra- 1',3',5'(10'), 16'-tetraen-7'α-yl) undecanamide (15) ( 244 mg, 80%) as colorless oil; $^1$H-NMR $δ_m(CDCl_3)$ 0.92 (s,3H,18' -$CH_3$), 0.92 and 0.95 (2t,3H,J=7.0 Hz,N$(CH_2)_3C\underline{H}_3$), 2.18 (s,3H, 17'-$OCOCH_3$), 2.28(s,3H,3'-OCOCH $_3$), 2.76 app (d,1H,J=16.1 Hz, part of ABX system,6'-H), 2.90 and 2.96 (2s,3H,N—$CH_3$), 3.26 and 3.35 $(2t_{app},2H,J=7.6$ Hz,N— $CH_2$—), 5.52

(m,1H,16'-H), 6.80 (broad s,1H,4'-H), 6.85 (dd,1H,$J_1$=9.1 Hz and $J_2$=3.0 Hz,2'-H), 7.27 (d,1H,J=9.1 Hz,1'-H); IR $v_{max}$(neat) 1750, 1635, 1200 cm$^{-1}$; MS m/e 607 (M$^+$,2%), 5(M$^+$-2COCH$_2$,100%), 550 (M$^+$-COCH$_2$—CH$_3$,13%), 523 (M$^+$2-COCH$_2$,45%), 142 (C$_2$H$_4$CON(CH$_3$)C$_4$H$_9^+$,55%), 129 (C$_4$H$_9$(CH$_3$)NCOCH$_3^+$,38%), 114 (C$_4$H$_9$(CH$_3$)NCO$^+$, 60%), 86 (C$_4$H$_9$(CH$_3$)N$^+$, 25%); EXACT MASS calcd for C$_{38}$H$_{57}$O$_5$N 607.4239, found 607.4234.

N-butyl, N-methyl-11-(16α-chloro-3'acetoxy- 17'-oxo-estra-1',3',4' (10')-triene-7'α-yl) undecanamide (16, X=Cl)

To diacetate amide 15, dissolved in 5 ml of acetone, was added solution of sodium acetate (2.6 equivalents) in acetic acid and water (1:11.3 v/v) and then, was treated with tertbutyl hypochlorite (1 eq.) prepared from t-butanol (4 ml) and Javel water (Javex 6.1%, 50 ml). The clear solution was warmed to 55° C. and stirred for 1 h. Afterwards, the solvent was evaporated to dryness. The residue was dissolved in ether (100 ml) and water was added (20 ml). The organic phase was washed with water, dried with anhydrous MgSO$_4$ and evaporated to dryness. The residue was purified by chromatography on silica gel carried out with mixture of EtOAc/hexane (3:7 v/v) to give the N-butyl, N-methyl-11-(16' α-chloro-3'-acetoxy-17'-oxo-estra-1',3',4' (10')-trien-7'α-yl) undecanamide 16, X=Cl) (115 mg, 89%) as colorless oil; $^1$H-NMR v (CDCl$_3$) 0.92 and 0.95 (2t,3H,J=7.0 Hz,N(CH$_2$)$_3$C$\underline{H}$ $_3$), 0.96 (s,3H,18'-CH$_3$), 2.28 (s, 3H,3'-OCOCH$_3$), 2.80 app (d,1H,J=16,6 Hz, part of ABX system, 6'-H) 2.90 and 2.96 (2s,3H,N—CH$_3$), 3.24 and 3.35 (2t $_{app}$, 2H,J=7.4 Hz,—N—CH$_2$—), 4.46 (d,1H,J=6.6 Hz,16'β-H), 6.82 (broad s, 1H,4'-H), 6.86 (dd,1H,J=9.1 Hz and $J_2$=,2.6 Hz,2'-H), 7.29 (d,1H,J= 9.1 Hz,1'-H); IR $v_{max}$ (neat) 1750, 1640, 1250 cm$^{-1}$; MS m/e 601, 599 (M$^+$,24%, 68%), 142 (C$_2$H$_4$CON(CH$_3$)C$_4$H$_9^+$ 100%), 114 (C$_4$H$_9$(CH$_3$)NCO$^+$, 93%).

N-butyl, N-methyl-11-(16α-chloro-3',17' -dihydroxy-estra-1',3',5'(10')-trien-7'α -yl) undecanamide ("EM 139") and ("EM 170")

A stirred solution of haloketone amide (16, X=Cl) in anhydrous tetrahydrofuran (THF) (10 ml) under argon was chilled to −70° C. with 2-propanol/dry ice bath. A solution of 1.0M of lithium aluminium hybride (2 eq.) was then added dropwise. After 30 min, the reaction was allowed to return slowly at 0° C. for 5 min, then was quenched by the dropwise addition of a mixture of THF-EtOAc (5 ml) (1:1 v/v) and acidified at pH~ 4 with (10%) HCl. The mixture was stirring for 5 min at room temperature and then extracted with EtOAc. The organic phase was washed with water, dried on anhydrous Na$_2$SO$_4$ and evaporated under reduced pressure. The residue was chromatographed on silica gel with a mixture of EtoOAc/hexane (4:6 v/v) as eluant:

N-butyl, N-methyl-11-(16'α-chloro-3'17'α -dihydroxy-estra-1',3',5'(10')-trien-7'α-yl) undecanamide ("EM 170")

(15 mg, 29%) as colorless oil; analytical sample was obtained by HPLC purification; $^1$H-NMR δ(CDCl$_3$, 400 MHz) 0.79 (s, 3H,18'-CH$_3$), 0.93 and 0.96 (2t, 3H,J=7.3 Hz,N(CH$_2$)$_3$CH $_3$), 2.80 (2H,$J_{6,6}$=17.1 Hz and $J_{6,7}$= 4.5 Hz, Δδ=24.34 (Hz, system ABX, 6'-H), 2.94 and 2.99 (2s, 3H,N—CH$_3$), 3.26 (dd,$J_1$=7.6 Hz and $J_2$=7.4 Hz) and 3.32–3.43 (m)-[2H,—N—CH$_2$—], 3.71 (d,1H,J=4.5 Hz,17'β-H), 4.63 (ddd, 1H, $J_{16,15}$=10.2 Hz, $J_{16,17}$ =4.5 Hz and $J_{16,15}$3.9 Hz, 16'β-H), 6.50 (d, 1H, J= 24 Hz, 3'-OH), 6.60 (d, 1H,J=2.5 Hz, 4'-H) 6.66 (dd,1H, $J_1$=8.4 Hz and $J_2$=2.5 Hz, 2'-H), 7.14 (d,1H,J=8.5 Hz, 1'-H); IR $v_{max}$(neat) 3300, 1615, 1495 cm$^{-1}$; MS m/e 561,559 (M$^+$, 40%, 100%), 523 (M$^+$-HCl, 20%), 142 (C$_2$H$_4$CON(CH$_3$)C$_4$ H$_9^+$, 44), f 114 (C$_4$H$_9$(CH$_3$)CNO$^+$, 37%); Exact mass calculated for C$_{34}$H$_{54}$O$_3$N$^{35}$Cl 559.3785, found 559.3821;

and

-N-butyl, N-methyl-11-(16'α-chloro-3',17'β -dihydroxy-estra-1'3',5'(10')trien- 7'α-yl) undecanamide ("EM 139")

(25 mg, 55%) as a colorless oil; analytical sample was obtained by HPLC purification; 1H-NMR δ(CDCl$_3$, 400 MHz), 0.81 (s,3H, 18'-CH$_3$), 0.93 and 0.96 (2t, 3H,J=7.3 Hz, (CH$_2$)$_3$CH $_3$), 2.78 (2H, $J_{6,6}$=16.2 Hz and $J_{6,7}$= 4.5 Hz, Δ$^5$=24.34 Hz, system ABX, 6'-H), 2.94 and 2.99 (2s, 3H,N—CH$_3$), 3.27 (dd, $J_1$=7.6 Hz and $J_2$7.5 Hz) and 3.31–3.45 (M) [2H, —N—CH$_2$—], 3.86 (dd, 1H, $J_{17,17}$-OH=3.4 Hz and $J_{17,16}$=5.9 Hz, 17'α-H), 4.11 (ddd, 1H, $J_{16,15}$=10.8 Hz, $J_{16,17}$=5.9 Hz and 4.11 (ddd, 1H, $J_{16,15}$=10.8 Hz, $J_{16,17}$= 5.9 Hz and $J_{16,15}$=2.5 Hz, 16'β -H), 6.56 (d, 1H, J=19.7 Hz, 3'-OH), 6.61 (d, 1H, J=2.5 Hz, 4'-H), 6.66 (dd, 1H, $J_1$=8.4 Hz and $J_2$=2.6 Hz, 2'-H), 7.13 (d, 1H, J=8.4 Hz, 1'-H); IR $v_{max}$(neat) 3320, 1615, 1490 cm$^{-1}$; MS m/e 561,559 (M$^+$, 38%, 100%), 523 (m$^+$-HCl, 16%), 142 (C$_2$H$_4$CON(CH$_3$)C$_4$H$_9^+$, 80%), 114 (C$_4$H$_9$(CH$_3$)CNO$^+$, 76%); exact mass calculated for C$_{34}$H$_{54}$O$_3$N$^{35}$Cl 559.3785, found 559.3825.

Scheme 3

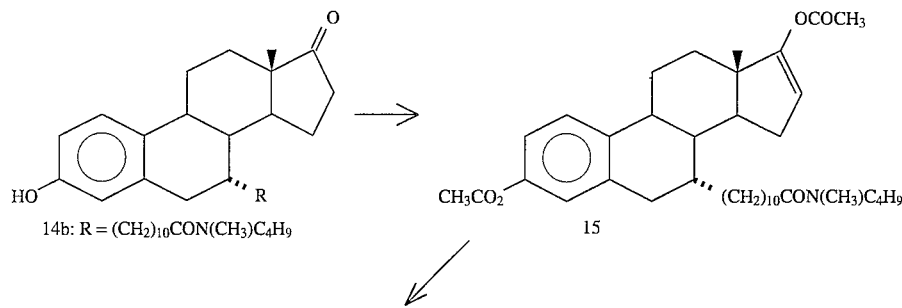

14b: R = (CH$_2$)$_{10}$CON(CH$_3$)C$_4$H$_9$

15

-continued
Scheme 3

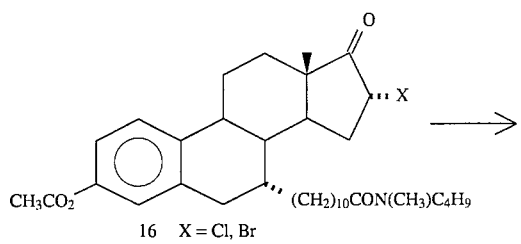 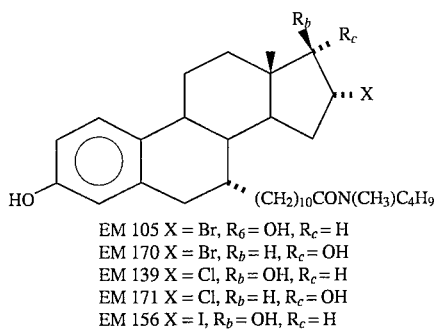

16  X = Cl, Br

EM 105 X = Br, $R_b$ = OH, $R_c$ = H
EM 170 X = Br, $R_b$ = H, $R_c$ = OH
EM 139 X = Cl, $R_b$ = OH, $R_c$ = H
EM 171 X = Cl, $R_b$ = H, $R_c$ = OH
EM 156 X = I, $R_b$ = OH, $R_c$ = H

N-n-butyl, N-methyl-11-(16'α-bromo-3'-acetoxy-17'-oxo-estra-1',3',5'(10'),trien-7'α-yl) undecanamide (16, X=Br)

To the above diacetate 15 (244 mg, 0.40 mmol) dissolved 10 ml of acetic acid was added dropwise with stirring within 10 minutes and a room temperature, a brominating solution composed of 50 mg (0.6 mmol) of sodium acetate, 1.6 ml of acetic acid, 0.04 ml of water and 63.9 mg (0.02 ml, 0.04 mmol) of bromine. During the course of this reaction, a red coloration appeared and disappeared. To the solution, 50 ml of ether was added and the organic phase was washed with water (4×50 ml) followed by a saturated sodium bicarbonate solution (2×50 ml) and finally with water (3×50 ml). The combined phase was dried over anhydrous magnesium sulfate and the solvent was removed in vacuo. The residue was chromatographed on silica gel (Kieselgel, 60F254, Merck, 0.063–0.200 mm) Elution with a mixture of hexane-ethyl acetate (4:1 v/v) yielded N-butyl, N-methyl-11-(16α-bromo-3'-acetoxy-17'-oxo-estra-1',3',5'(10'),trien-7'-α-yl) undecanamide (16, X=Br) (201 mg, 78%) as colorless oil (201 mg, 78%), as colorless oil; $^1$H-NMR o (CDCl$_3$), 0.94 (s, 3H,18'-CH$_3$), 2.28 (s, 3H, 3'-OCOCH$_3$), 2.82 app (d,1H,J= 16.4 Hz, part of ABX system, 6'-H), 2.90 and 2.96 (2s, 3H,N—CH$_3$), 3.24 and 3.35 (2t$_{app}$, 2H, J=7.7 Hz, —N—CH$_2$—), 4.58 (t,1H,J=3.6 Hz, 16 β-H), 6.82 (broad 1H,4'-H), 6.88 (dd,1H, J=8.0 Hz and J$_2$=4.0 Hz,2'-H), 7.29 (d,1H,J=8.0 Hz, Hz, 1'-H); MS m/e 644 (m$^+$,7%), 565 (M$^+$—Br, 77%), 522 (m$^+$—Br—COCH$_2$, 55%), 142 (C$_2$H$_4$CON(CH$_3$)C$_4$H$_9$, 67%) 114 (C$_4$H$_9$(CH$_3$)NCO$^+$, 66%), 88 (100%).

N-butyl, N-methyl-11-(16'α-bromo-3',17'-dihydroxy-estra-1',3,4'(10')trien-7'α-yl) undecanamide ("EM 105") and ("EM 171")

A solution of bromoketone amide 16 (X=Br) (295 mg, 0.46 mmol) in anhydrous tetrahydrofuran (10 ml) under argon was chilled to −70° C. and a solution of 1.0M of lithium aluminium hybride in ether (0.92 ml, 0.92 mmol) was added dropwise with rapid magnetic stirring. After 30 min, the reaction was quenched by the dropwise addition of a mixture of THF-ethyl acetate (1:1 v/v) and acidified by 10% hydrochloric acid. The mixture was stirring for 5 min at room temperature and then extracted with ethyl acetate. The organic phase was washed with water, dried on anhydrous sodium sulfate and evaporated to dryness under reduced pressure. The residue was purified by chromatography on silica gel. Elution with a mixture of hexane-ethyl acetate (7:3 v/v) gave:

N-n-butyl, N-methyl-11-(16'α-bromo-3',17'α-dihydroxy-estra-1',3',5'(10')-trien-7'α-undecanamide ("171")

(63 mg, 21%) as colorless oil; $^1$H-NMR δ(CDCl$_3$400 MHz) 0.81 (s, 3H, 18'-CH$_3$), 0.93 and 0.96 (2t, 3,J=7.3 Hz,N(CH$_2$)$_3$CH$_3$), 2.79 (2H,J$_{6,6}$=16.6 Hz, J$_{6,7}$=4.7 Hz, =Δδ=24.34 Hz, system ABX, 6'-H), 2.94 and 2.99 (2s,3H, N—CH$_3$), 3.27 (dd,2H,J$_1$=7.7 Hz and J$_2$=7.5 Hz, —N—CH$_2$—), 3.31–3.44 (m,2H,—N—CH$_2$—), 3.66 (dd, 1H,J$_{17,17}$=1.4 Hz, J$_{17,16}$=4,3 H 17'β-H), 4.68 (dt,1H,J$_{16,17}$= 4,3 Hz, m, J$_{16,15}$=9.7 Hz, 16'β-H), 6.60 (d,1H,J=2.4 Hz, 4'-H), 6.65 (dd, 1H,J=8.5 Hz and J$_2$=2.5 Hz, 2'-H), 7.14 (d,1H,J=8.5 Hz, 1'-H); IR ν$_{max}$ (neat) 3300, 1615, 1495 cm$^{-1}$; MS m/e 605,603 (M$^+$, 17%), 523 (M$^+$-HBr, 81%), 142 (C$_2$H$_4$CON(CH$_3$)C$_4$H$_9$$^+$100%), 114 (C$_4$H$_9$ (CH$_3$)NCO$^+$, 97%); Exact mass calculated for C$_{34}$H$_{54}$O$_3$N$^{79}$Br 603.8289, found 603.3304. and N-n-butyl, N-methyl-11-(16'α-bromo-3',17'β-dihydroxy-estra-1',3',5=(10')-trien-7α-yl) undecanamide ("EM 105")

(170 mg, 50%) as a colorless oil; analytical sample was obtained by HPLC purification; $^1$H-NMR δ(CDCl$_3$, 400 MHz), 0.80 (s,3H,18'-CH$_3$), 0.93 and 0.96 (2t,3H,J=7.3 Hz,N(CH$_2$)$_3$CH$_3$), 2.80 (2H,J$_{6,6}$=16.4, J$_{6,7}$=4.6 Hz, Δδ=24.34 Hz, system ABX, 6'-H), 2.94 and 2.99 (2s,3H, N—CH$_3$), 3.27 (dd, 2H,J$_1$=7.7 Hz and J$_2$=7.5 Hz, —N—CH$_2$—), 3.31–3.45 (m,2H,—N—CH$_2$—), 4.02 (dd, 1H,J$_{17,17}$=3.7 Hz, and J$_{17,16}$=6.1 Hz, 17'α-H), 4.15 (ddd,1H, J$_{16,15}$=10.2 Hz, J$_{16,17}$=6.1 Hz and J$_{16,15}$=2.9 Hz, 16'β-H), 6.61 (d,1H,J=2.5 Hz, 4'-H), 6.66 (dd,1H,J=8.4 Hz and J$_2$ 2.5 Hz, 2'-H), 7.12 (d,1H,J=8.4 Hz, 1'-H); IR ν$_{max}$ (neat) 3320, 1610, 1490 cm$^{-1}$; MS m/e 605, 603 (M$^+$, 29%), 523 (M$^+$-HBr, 100%), 142 (C$_2$H$_4$CON(CH$_3$)C$_4$H$_9$$^+$, 70%), 114 (C$_4$H$_9$(CH$_3$)NCO$^+$, 60%); Exact mass calculated for C$_{34}$H$_{54}$O$_3$N$^{79}$Br 603.3289, found 603.3289.

Antiestrogens useful in the combination therapy of the invention include but are not limited to Tamoxifen, commercially available from Imperial Chemical Industries, and EM 139, EM 170 and EM 171 whose synthesis are set forth above. Some steroidal antagonists also function as inhibitors of sex steroid formation. The antiestrogens EM 139, EM 170 and EM 171, for example, exhibit the dual function of acting as sex steroid formation inhibitors. For this reason, a combination therapy requiring both an inhibitor of sex steroid formation and a steroidal antagonist may be produced by administering a single active compound (alone or together with diluent) capable of performing both functions. Another example of a dual function active ingredient is the antiandrogen EM 101 which has al shown an inhibitory effect on sex steroid formation.

The inhibitor of sex steroid biosynthesis is preferably capable of acting at least in peripheral tissues (extra-testicular and extra-adrenal). In preferred embodiments, it is used in association with an antiandrogen, and with an LHRH agonist. The use of an LHRH agonist is the more preferred method of chemical castration. Surgical castration may alternatively be used as a means of inhibiting testicular hormonal secretions, but chemical castration is preferred.

By the term "LHRH agonist" is meant synthetic analogues of the natural luteinizing hormone-releasing hormone (LHRH), a decapeptide of the structure: L-pyroglutamyl-L-histidyl-L-tryptophyl-L-seryl-L-tyrosyl-glycyl-L-leucyl-arginyl-L-prolyglycyl-$NH_2$.

Typical suitable LHRH agonists include nonapeptides and decapeptides represented by the formula: L-pyroglutamyl-L-histidyl-L-tryptophyl-L-seryl-L-tyrosyl-X-Y-L-arginyl-L-prolyl-Z wherein X is D-tryptophyl, D-leucyl, D-alanyl, iminobenzyl-D-histidyl, 3-(2-naphthyl)-D-alanyl, O-terbutyl-D-seryl, D-tyrosyl, D-lysyl, D-phenylalanyl or N-methyl-D-alanyl and Y is L-leucyl, D-leucyl, $N^\alpha$-methyl-D-leucyl, $N^\alpha$-methyl-L-leucyl or D-alanyl and wherein Z is glycyl-$NHR_1$ or $NHR_1$ wherein $R^1$ is H, lower alkyl or lower haloalkyl. Lower alkyl includes, for example, methyl, ethyl, propyl, pentyl, hexyls, iso-butyl, neopentyl and the like. Halolowleralkyl includes, for example, —$CF_3$, —$CH_2CF_3$, —$CF_2CH_3$, and the like. Fluorine is a preferred halogen.

Preferred nonapeptides wherein Y is L-leucyl and X is an optically active D-form of selected amino acids and Z is $NHC_2H_5$ are [D-Trp$^6$, des-Gly-$NH_2^{10}$]LHRH ethylamide (X=D-Trp$^6$); [D-Ser-t-BuO)$^6$, des-Gly-$NH_2^{10}$]LHRH ethylamide [X-D-Ser(t-BuO$^6$)]; [D-Leu$^6$, des-Gly-$NH_2^{10}$]LHRH ethylamide (X=D-Leu$^6$, [D-His(Bzl)$^6$, des-Gly-$NH_2^{10}$]LHRH ethylamide (X=iminobenzyl-D-His$^6$) and [D-Ala$^6$, des-Gly-$NH_2^{10}$]-LHRH ethylamide (X=D-Ala$^6$).

Preferred decapeptides include [D-Trp$^6$]LHRH wherein X=D-Trp, Y=L-leucyl, Z=glycyl-$NH_2$, [D-Phe$^6$]-LHRH wherein X=D-phenylalanyl, Y=L-leucyl and Z=glycyl-$HN_2$) or [D-Nal(2)$^6$]LHRH which is [$^{93}$-3-(2-naphthyl)-D-Ala$^6$] LHRH wherein X=3(2-naphthyl)-D-alanyl, Y=L-leucyl and Z=glycyl-$NH_2$.

Other LHRH agonists useful within the scope of this invention are the α-aza analogues of the natural LHRH, especially, [D-Phe$^6$, Azgly$^{10}$]-LHRH, [D-Tyr(-Me)$^6$, Azgly$^{10}$]LHRH, and [D-Ser-(t-BuO)$^6$, Azgly$^{10}$]LHRH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LHRH antagonists include [N-Ac-D-p-Cl-Phe$^{1, 2}$, et al., Biochem. Biophys. Res. Commun. 100, 915–920 (1981); [N-Ac-D-p-Cl-Phe$^{1,2}$, D-Trp$^3$, D-Arg$^6$, D-Ala$^{10}$]LHRH disclosed by D. H. Coy et al., Endocrinology, 110: 1445–1447 (1982); [N-Ac-D-(3-(2-naphthyl)-OAla)$^1$, D-p-Cl-Phe$^2$, D-Trp$^3$, D-hArg(Et$_2$)$^6$, D-Ala$^{10}$] LHRH and [N-Ac-Pro$^1$, D-pF-Phe$^2$, D-(3-(2-naphthyl)-Ala$^{3,6}$]-LHRH disclosed by J. J. Nestor et al. J. Steroid Biochem., 20 9no. 6B), 1366 (1984); the nona- and decapeptide analogs of LHRH useful as LHRH antagonists disclosed in U.S. Pat. No. 4,481,190 (J. J. Nestor et al.); analogs of the highly constrained cyclic antagonist, cycle [Δ$^{3\ Pro1}$, D-p-Cl-Phe$^2$, D-Trp$^{3,6}$, N-Me-Leu$^7$, ≠-Ala$^{10}$]-LHRH disclosed by J. Rivier, J. Steroid Biochem., 20 (no. 6B), 1365 (1984) and [N-Ac-D-(3-(2-naphthpyl)-Ala$^1$, D-p-F-Phe$^2$, -Trp$^3$, D-Arg$^6$]LHRH disclosed by A. Corbin et al., J. Steroid Biochem. 20 (no. 6B) 1369 (1984).

Other LHRH agonist and antagonist analogs are disclosed in LHRH and its Analogs (B. H. Vickery et al. eds, at pages 3–10 (J. J. Nestor), 11–22 (J. Rivier et al.) and 22–33 (J. J. Nestor et al.) as well as in The Case for LHRH agonists (Clinical Oncology, Furr and Denis, eds), Bailliere Tindall, vol. 2, no. 3, pp. 559–570, 1988).

The LHRH agonists and antagonists useful in this invention may conveniently be prepared by the method described by Stewart et al. in "Solid Phase Peptide Synthesis" (published in 1969 by Freeman & Co., San Francisco, page 1) but solution phase synthesis may also be used.

The nona- and decapeptides used in this invention are conveniently assembled on a solid resin support, such as 1% cross-linked Pro-merrifield resin by use of an automatic peptide synthesizer. Typically, side-chain protecting groups, well known to those in the peptide arts, are used during the dicyclohexylcarbodiimidecatalyzed coupling of a tert-butyloxycarbonylamino aci to the growing peptide attached to a benzhydrylamide resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration and partition chromatography and optionally lyophilization. See also D. H. Coy et al., J. Med. Chem. 19, pages 423–425 (1976).

In this invention, the LHRH agonist or antagonist, the 5α-reducta inhibitor, the antiandrogen, the antiestrogen, and, where applicable, the inhibitor of 3β- and 17β-hydroxysteroid dehydrogenas activities are administered as pharmaceutical compositions via topical, parenteral or oral means. The LHRH agonist or antagonist is administered parenterally, i.e., intramuscularly, subcutaneously or intravenously by injection or infusion by nasal drops or by suppository. The LHRH agonist or antagonist may also be microencapsulated in or attached to a biocompatible, biodegradable polymer, e.g., poly(d,l-lactide-co-glycolide) and subcutaneously or intramuscularly injected by a technique called subcutaneous or intramuscular depot to provide continuous, slow release of the LHRH agonist or antagonist over a period of 30 days or longer. The most preferred route of administration of the LHRH agonist or antagonist is subcutaneous or intramuscular depot injection. Preferably the antiestrogen will be administer orally. Preferably, the 5α-reductase inhibitor, the antiandrogen, the antiestrogen, the inhibitor of 3β-HSD and the inhibitor of 17 -HSD can also be administered orally. The antiestrogen, an inhibitor of 3β-HSD and inhibitor of 17β-HSD can also be administered in slow release formulation, e.g. poly(d,l-lactide-coglycolide) or as implants.

The amount of each component administered is determined by the attending clinicians taking into consideration the etiology and severity of the disease, the patient's condition and age, the potency of each component and other factors. According to this invention, the following dosage ranges are suitable.

The LHRH agonist or antagonist is generally administered at from about 10 to 5000 μg per day with contemplated dosage ranges of about 10 to 1500 μg per day and about 250 (preferably 50 μg to 500 μg per day) for the LHRH agonist and to about 100 to 2000 μg per day for the LHRH antagonist being preferred.

In the most preferred embodiment of this invention, the LHRH agonist or antagonist is administered subcutaneously in a daily dose of 500 μ for the first 30 days and thereafter subcutaneously in a daily dose of 250 μg regardless of the patients' body weight. When the LHRH agonist or antagonist is administered, once every 30-day period is used, with a dose of 750 to 15,000 μg per 30-day period being preferred. Similar daily delivery doses are used for longer-term controlled release formulations.

The inhibitors of 3β-HSD and 17β-HSD are preferably administered in dosages ranging from about 0.1 to 25 mg/kg per day with 200 mg per day in two equally divided doses being preferred.

The antiestrogen compositions are administered in a dosage range of about 0.05 to 25 mg/kg body weight per day, with 20 mg, especially 40 mg, in two equally divided doses being preferred.

The 5α-reductase inhibitor compositions are administered in a dosage ranging from 0.1 to 25 mg/kg per day with 50 mg per day in two equivalent doses being preferred.

The antiandrogen and aromatase inhibitor compositions are administered in a dosage range of 0.5 to 25 mg/kg body weight per day with 750 mg per day in three equally divided doses being preferred.

The LHRH agonist or antagonist, antiestrogen, antiandrogen, an inhibitor of aromatase, 17β-HSD and 3β-HSD each may be administered separately or when the modes of administration are the same, all or at least two of them may be administered in the same composition, but in any case the preferred ratio of LHRH agonist to antiestrogen, to antiandrogen to inhibitor of 17β-HSD and administered daily will be about 250 μg of LHRH agonist to about 750 mg of antiandrogen, about 40 mg of antiestrogen, to about 40 mg of inhibitor of 17β-HSD and about 40 mg of inhibitor of 3β-HSD.

In the therapy of prostate cancer, combining the administration of an LHRH agonist or antagonist, an antiestrogen, an antiandrogen and an inhibitor of 17β-HSD, the dosages preferable are as follows: the LHR agonist or antagonist is generally administered at from about 10 to 2000 μg per day, with contemplated dosage ranges of 10 to 500 μg per day, 50– 250 μg per day and 250 to 500 μg per day being preferred In the most preferred embodiment of this aspect of this invention, the LHRH agonist or antagonist is administered subcutaneously in a daily dose of 500 μ for the first 30 days and thereafter subcutaneously in a daily dose of 250 μg regardless of the patients' body weight. When the LHRH agonist or antagonist is administered, once every 30-day period, by intramuscular or subcutaneous depot injection, a dose from about 300 to 60000 (occasionally 10000) μg per 30-day period is used, with a dose of 750 2000 μg per 30-day period being preferred. The antiandrogen composition is generally administered in a dosage range of about 0.5 to 25 mg/kg (body weight) per day with 400 especially 750 mg per day in three equally divided doses being preferred. The antiestrogen and inhibitor of 17β-HSD and 3β-HSD activities are administered in a dosage range of about 0.1 to 25 mg/kg body weight per day, with 100 mg in two, preferably with 50 mg in two, equally divided doses being preferred.

The LHRH agonist or antagonist, antiandrogen, antiestrogen, 5 α-reductase inhibitor, inhibitor of 17β-HSD, inhibitor of 3β-HSD, inhibitor of aromatase, each may be administered separately or when the modes of in the same composition, but in any case the preferred ratio of LHRH agonist to antiandrogen to antiestrogen administered daily will be about 750 μg of LHRH agonist to about 250 mg of antiandrogen to preferably 40 mg of antiestrogen.

In the therapy of prostate cancer, according to this invention, it is preferred that the LHRH agonist is [D-Trp$^6$, des-Gly-NH$_2^{10}$] LHRH ethylamide be administered subcutaneously in single daily dose of 500 μg for the first thirty (30) days of treatment and thereafter in a single daily dose of 250 μg.

In the combination therapy of prostate cancer according to this invention, the administration of the antiandrogen, antiestrogen, inhibitor of 17β-HSD, inhibitor of 5α-reductase, inhibitor of aromatase, and inhibitor of 3β-HSD, LHRH agonist or LHRH antagonist can be started any order of sequence. Preferably, the administration of the antiandrogen and 5α-reductase inhibitor, are started before (preferably two to four hours before) the administration of the LHRH agonist or LHRH antagonist is started. Orchiectomy can replace LHRH agonist or antagonist. Preferably, the administration of the inhibitor of 17β-HSD and inhibitor of 3β-HSD is started on the same day as the administration of the LHRH agonist or LHRH antagonist. However, the attending clinician may elect to start administration of the LHRH agonist or antagonist simultaneously with the antiandrogen, antiestrogen inhibitor of 17β-HSD and inhibitor of 3β-HSD.

When patients whose testes have already been surgically removed are treated according to this invention, the administration and dosage of the antiandrogen and the other components of the therapy (except the LHRH agonist or antagonist which is not used) are the same as indicated for the therapy in which the LHRH agonist or antagonist is used.

The LHRH agonists or antagonists useful in the present invention are typically amorphous solids which are freely soluble in water or dilute acids, e.g., HCl, H$_2$SO$_4$, citric, acetic, mandelic or fumaric. The LHRH agonist or antgonist for subcanteous injection is supplied in vials containing 5 ml of sterile solution with the LHRH agonist or antagonist at a concentration of about 1.0 mg/ml.

A typical pharmaceutical composition of the LHRH agonist or antagonist includes the LHRH agonist or antagonist or a pharmaceutically acceptable acid salt thereof, benzyl alcohol, a phosphate buffer (pH 6.0–6.5) and sterile water.

The LHRH agonist or antagonist for intramuscular or subcutaneous depot injection may be microencapsulated in a biocompatible, biodegradable polymer, e.g., poly (d,1-lactide-co-glycolide) by a phase separation process or formed into a pellet. The microspheres may then be suspended in a carrier to provide an injectable preparation or the depot may be injected in the form of a pellet. See also European patent application EPA No. 58,481 published Aug. 25, 1982 for solid compositions for subdermal injection or implantation or liquid formulations for intramuscular or subcutaneous injections containing biocompatible, biodegradable polymers such as lactide-glycolide copolymer and an LHRH agonist, e.g. D-Ser-t-BuO $^6$, Azgly$^{10}$-LHRH. These formulations permit controlled release of the peptide.

The inhibitors of 17β-HSD, 3β-HSD, aromatase and 5α-reductase are typically compounded in customary ways for oral administration, e.g., in tablets, capsules and the like. These compounds useful in the present invention are typically formulated with conventional pharmaceutical excipient e.g., spray dried lactose and magnesium stearate into tablets or capsules for oral administration. The antiestrogens, when used with the invention, are typically compounded in customary ways for oral administration e.g., in capsules, tablets, as degrees or even in liquid form, e.g., suspensions or syrups. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste-improving substances can be added in the case of oral administration forms. The therapeutically active antiestrogen compound should be present in a concentration of about 0.5–90% by weight of the total mixture, i.e., in amounts that are sufficient for maintaining the above-mentioned dosage range.

As further forms, one can use plug capsules, e.g., of hard gelatin, as well as closed soft-gelatin capsules comprising a softener or plasticizer, e.g. glycerine. The plug capsules contain the active substance preferably in the form of granulate, e.g., in mixture with fillers, such as lactose, saccharose, mannitol, starches, such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil. One or more of the active substances (antiestrogen or inhibitor of 17β-HSD and 3β-HSD can be microencapsulated in or attached to a biocompatible, biodegradable polymer, e.g. poly(d,l-lactide-co-glycolide) and subcutaneously or intramuscularly injected by a technique called subcutaneous or intramuscular depot to provide continuous slow release of the compound(s) for a period of 2 weeks or longer.

In the most preferred aspect of this invention, the LHRH agonist is [D-Trp$^6$, des-Gly-NH$_2$$^{10}$] LHRH ethylamide which is administered subcutaneously in single daily dose of 500 μg for the first thirty (30) days treatment and thereafter in a single daily dose of 250 μg: the antiandrogen is EM 101 which is administered orally in three equally divided daily doses of 250 mg; and the inhibitor of sex steroid biosynthesis is EM 139 and/or MK 906 administered orally in two equally divided doses of 50 mg every 12 hours.

The inhibitor(s) of sex steroid biosynthesis and the antiandrogen are preferably administered to a male in need of the prostate cancer treatment of this invention two to four hours before the LHRH agonist or antagonist is administered, but the attending clinician may elect to start administration of the LHRH agonist or antagonist, the antiandrogen and the inhibitor of steroid biosynthesis simultaneously. When the antiandrogen and sex steroid inhibitor are particularly effective, both chemical (LHRH agonist or antagonist) and surgical castration may be avoided. Especially, when patients whose testes have already been surgically removed are treated according to this invention, no LHRH agonist or antagonist need to be used but other dosages remain the same.

The terms and descriptions used herein are preferred embodiments set forth by way of illustration only, and are not intended as limitations on the many variations which those of skill in the art will recognize to be possible in practicing the present invention as defined by the following claims.

I claim:

1. A kit comprising a plurality of separate containers, wherein at least one of said containers contains at least one active ingredient which is distinct from all active ingredients contained in at least one other of said containers, wherein at least one of said containers contains an antiandrogen and at least one of said containers contains at least one compound which is a sex steroid formation inhibitor which does not suppress adrenal activity and which inhibits an enzyme that catalyzes a step in the synthesis of sex steroids from sex steroid precursors in peripheral tissues, wherein said inhibitor is selected from the group consisting of an inhibitor of 5α-reductase, an inhibitor of 17β-hydroxysteroid dehydrogenase and an inhibitor of 3β-hydroxysteroid dehydrogenase.

2. The kit, as recited in claim 1, wherein at least one container of said kit contains a pharmaceutical diluent or carrier.

3. The kit, as recited in claim 1, wherein at least one container of said kit contains at least one active ingredient selected from the group consisting of an inhibitor of testicular hormonal secretions, an inhibitor of aromatase and an antiestrogen.

4. The kit, as recited in claim 1, wherein at least one container of said kit contains an LHRH agonist or antagonist.

5. The kit, as recited in claim 1, wherein an antiandrogen is present in least one container of said kit and an inhibitor of 5α-reductase is present in at least one container of said kit.

6. The kit, as recited in claim 1, wherein an antiandrogen is present in at least one container of said kit, an inhibitor of 5α-reductase is present in at least one container of said kit and an inhibitor of aromatase is present in at least one container of said kit.

7. The kit, as recited in claim 1, wherein an antiandrogen is present in at least one container of said kit, an inhibitor of 5α-reductase is present in at least one container of said kit, an inhibitor of aromatase is present in at least one container of said kit and an LHRH agonist or antagonist is present in at least one container of said kit.

8. The kit, as recited in claim 1, wherein an antiandrogen is present in at least one container of said kit and an inhibitor of 17β-hydroxysteroid dehydrogenase is present in at least one container of said kit.

9. A kit, comprising a plurality of separate containers, wherein at least one of said containers contains at least one active ingredient which is distinct from all other active ingredients contained in at least one other of said containers, wherein at least one of said containers contains at least one compound which is a sex steroid formation inhibitor which does not suppress adrenal activity and which inhibits an enzyme that catalyzes a step in the synthesis of sex steroids from sex steroid precursors in peripheral tissues, and wherein at least one of said containers contains an antiandrogen having, as part of its molecular structure, a substituted or unsubstituted androgenic nucleus of the formula:

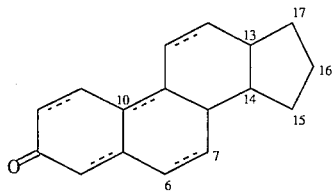

wherein the dotted line represents an optional double bond; and said antiandrogen having as another part of its molecular structure, at least one side chain represented by the formula: —R¹[—B—R²—]ₓL—G, said chain being substitued onto said androgenic nucleuus at a position substituted onto said androgenic nucleus at a position selected from the group consisting of 6α, 7α, 14α, 15α, 16α and 17, wherein:

x is an integer from 0 to 6, wherein at least one of L and G is a polar moiety distanced from said ring carbon by at least three intervening atoms, and wherein:

R¹ and R² are independently either absent or selected from the group consisting of straight or branched-chain alkylene, straight or branched-chain alkenylene straight or branched-chain alkynylene, phenylene and fluoro-substituted analogs of the foregoing;

B is either absent or selected from the group consisting of —O—, —S—, —SO—, —SO₂—, —NR³—, —CR³OR³—, and phenylene (R³ being hydrogen or lower alkyl);

L is selected from the group consisting of lower alkyl, —CONR⁴—, —CSNR⁴—, —NR⁵CO—, —NR⁵CS—, —NR⁵CONR⁴—, —SO₂NR⁴—, —NR⁵SO₂—, —NR⁴—, —S—, —SO—, —SO₂—, and a moiety which together with G, forms a heterocyclic ring having at least one nitrogen atom (R⁴ and R⁵ being independently selected from the group consisting of hydrogen and lower alkyl); and G is selected from a group consisting of hydrogen, lower alkyl, lower alkenyl, lower alkynyl, (C₃–C₇)cycloalkyl, bromo(lower)alkyl, chloro(lower)alkyl, fluoro(lower)alkyl, cyano(lower)alkyl, carboxyl(lower)alkyl, (lower)alkoxycarbonyl-(lower)alkyl, (C₆–C₁₀)aryl, (C₇–C₁₁)-arylalkyl, di(lower)alkylamino(lower)alkyl, fluoro-substituted analogs of the foregoing and a moiety which together with L forms a heterocyclic ring having at least one nitrogen atom.

10. The kit, as recited in claim 9, wherein at least one container of said kit contains a pharmaceutical diluent or carrier.

11. The kit, as recited in claim 9, wherein at least one container of said kit contains at least one active ingredient selected from the group consisting of an inhibitor of testicular hormonal secretions, an inhibitor of aromatase and an antiestrogen.

12. The kit, as recited in claim 9, wherein at least one container of said kit contains an LHRH agonist or antagonist.

13. The kit, as recited in claim 9, wherein an antiandrogen is present in at least one container of said kit and an inhibitor of 5α-reductase is present in at least one container of said kit.

14. The kit, as recited in claim 11, wherein an antiandrogen is present is at least one container of said kit, an inhibitor of 5α-reductase is present in at least one container of said kit and an inhibitor or aromatase is present in at least one container of said kit.

15. The kit, as recited in claim 9, wherein an antiandrogen is present in at least one container of said kit and an inhibitor of 17β-hydroxysteroid dehydrogenase is present in at least one container of said kit.

* * * * *